US008710246B2

(12) United States Patent
Åsberg et al.

(10) Patent No.: US 8,710,246 B2
(45) Date of Patent: Apr. 29, 2014

(54) SUBSTITUTED THIOPHENE PENTAMERS

(75) Inventors: Peter Åsberg, Stockholm (SE); Leif Johansson, Linköping (SE); Anna Herland, Solna (SE); Andreas Åslund, Linköping (SE); Peter Konradsson, Skänninge (SE)

(73) Assignee: Biochromix Newco AB, Stockholm (SE)

( * ) Notice: Subject to any disclaimer, the term of this patent is extended or adjusted under 35 U.S.C. 154(b) by 0 days.

(21) Appl. No.: 13/124,621

(22) PCT Filed: Oct. 19, 2009

(86) PCT No.: PCT/SE2009/051187
§ 371 (c)(1),
(2), (4) Date: Jan. 11, 2012

(87) PCT Pub. No.: WO2010/044743
PCT Pub. Date: Apr. 22, 2010

(65) Prior Publication Data
US 2012/0157516 A1    Jun. 21, 2012

(30) Foreign Application Priority Data

Oct. 17, 2008   (SE) .................................... 0850043
Oct. 23, 2008   (SE) .................................... 0850050

(51) Int. Cl.
C07D 409/14    (2006.01)
A61K 31/381   (2006.01)

(52) U.S. Cl.
USPC ........................................... 549/59; 514/444

(58) Field of Classification Search
USPC ........................................... 514/444; 549/59
See application file for complete search history.

(56) References Cited

U.S. PATENT DOCUMENTS 4,861,692 A   8/1989   Kuroda et al.
5,747,525 A   5/1998   Chang et al.

FOREIGN PATENT DOCUMENTS

| EP | 1 111 695 | 6/2001 |
| JP | 08-231536 | 9/1996 |
| WO | WO-98/23269 | 6/1998 |
| WO | WO-2005/109005 | 11/2005 |
| WO | WO 2007/091973 | * 8/2007 |
| WO | WO-2007/091973 | 8/2007 |
| WO | WO-2008/130296 | 10/2008 |

OTHER PUBLICATIONS

Rajkumer et al.; N. Engl. J. Med (2007), 356 (23); p. 2413-2415.*
Mangialasche et al., LancetNeurol. 2010; 9: p. 702-716).*
Destri et al. (Organic Electronics 3 (2002) 149-156).*
Bolvar-Marinez, L.E. et al., "Electronic Structure of Push-Pull Molecules Based on Thiophene Oligomers", Journal of Physical Chemistry, Jun. 27, 1996, vol. 100(26), Cover sheet and pp. 11029-11032.
Casanovas, Jordi et al., "Structural and electronic effects induced by carboxylic acid substitution in isomeric 2,2'=bithiophenes and oligothiophenes: A computational study", Polymer, Aug. 9, 2005, vol. 46, pp. 9452-9460, available online at www.sciencedirect.com.
Compound with CAS No. 732980-89-1, retrieved from the STN International File Registry database, Aug. 26, 2004 (date entered into STN database), 1 page.
De Oliveira et al., "Energy Gaps of [],[]'-Substituted Oligothiophenes from Semiempirical, Ab Initio, and Density Functional Methods", Journal of Physical Chemistry A, Aug. 12, 2000, vol. 104(35), cover sheet and pp. 8256-8262.
International Preliminary Report on Patentability for Intl. Pat. Appln. No. PCT/SE2009/051187, dated Apr. 19, 2011, 13 pp.
International Search Report and Written Opinion for Intl. Pat. Appln. No. PCT/SE2009/051187, mailed on Feb. 4, 2010, 21 pp.
Loewe, Robert S. et al., "A Simple Method to Prepare Head-to-Tail Coupled, Regioregular Poly(3-alkylthiophenes) Using Grignard Metathesis", Advanced Materials, 1999, vol. 11, No. 3, pp. 250-253.
Pina J., et al., "Photophysical Studies of a,w-Dicyano-oligothiophenes $NC(C_4H_2S)_nCN$ (n=1-6)", J. Phys. Chem. B, 2006, vol. 110, pp. 6499-6505.
Porzio, W. et al., "Functionalized Oligothiophenes for Optoelectronic Applications: 3',4',3'",4"-Tetra[(methoxycarbonyl)methyl]-2,2':5',2':5'Δ,2'-quinquithiophone and Related Polymers, Chemistry of Materials, 2005, vol. 17(2), cover sheet and pp. 242-249.
Rohde, Dirk et al., "Radical Ions of [], []'-Bis(diphenylamino)-capped Oligothiophenes: A Combined Spectroelectrochemical and Theoretical Study", Journal of Physical Chemistry B, Apr. 4, 2006, vol. 110(16), cover sheet and pp. 8223-8231.
Klingstedt, Therese et al., "Synthesis of a library of oligothiophenes and their utilization as fluorescent ligands for spectral assignment of protein aggregates," Org. Biomol. Chem., (2011), vol. 9, pp. 8356-8370.

* cited by examiner

Primary Examiner — Noble Jarrell
Assistant Examiner — Valerie Rodriguez-Garcia
(74) Attorney, Agent, or Firm — Foley & Lardner LLP

(57) ABSTRACT

A compound is provided of the formula

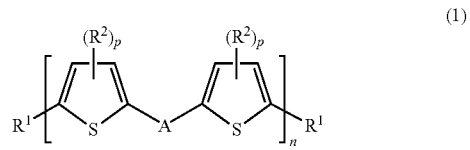

(1)

wherein each u is independently selected from 0 and 1; each $R^2$ and $R^4$ is independently selected from carboxy, carboxyalkyl, alkoxycarbonylalkyl, aminoalkyl, (amino)(carboxy)alkyl and (amino)(carboxy)alkoxy; or a pharmaceutically acceptable salt thereof.

8 Claims, 11 Drawing Sheets

SUBSTITUTED THIOPHENE PENTAMERS

CROSS-REFERENCE TO RELATED APPLICATIONS

This application is a national stage application of International Application Serial No. PCT/SE2009/051187, filed on Oct. 19, 2009, which claims the benefit of priority of Swedish Application No. 0850043-1 filed on Oct. 17, 2008 and Swedish Application No. 0850050-6, filed on Oct. 23, 2008, the contents of which are hereby incorporated by reference in their entireties.

FIELD OF THE INVENTION

The present invention relates to novel substituted thiophene derivatives useful in therapy, especially therapy of a mammal suffering from a disease involving misfolded or aggregated forms of proteins.

BACKGROUND OF THE INVENTION

Natural biopolymers, such as proteins, frequently have ordered conformations, such as alpha-helix and beta-sheets, which contribute to the three-dimensional ordered structure and the specific function of the biopolymer. The structure of a protein is essential for the protein's function; it has been shown by many scientists that an unfolded protein may not be functional. More important, in the last few years there is increasing awareness of the danger of protein misfolding and misassembly into for example amyloid and other pathological forms. Misfolding can change a protein from something that is useful into nonfunctional, harmful or even toxic. Human health relies on properly folded protein, and in vivo deposition of amyloid fibrils is associated with many diseases related to protein conformation, including Alzheimer's disease, Huntington's disease, systemic amyloidoses, and the prion diseases. The prion diseases, i.e. transmissible spongiform encephalopathy (TSE), in animals [e.g. bovine spongiform encephalopathy (BSE), Scrapie and chronic wasting disease (CWD)] and in humans [Creutzfeldt Jakob disease (CJD), Gerstmann-Sträussler-Scheinker disease (GSS), Kuru] are associated with the conformational conversion of the normal cellular prion protein, ($PrP^C$), to an infectious pathogenic disease-associated isoform denoted $PrP^{Sc}$. Proteins frequently alter their conformation due to different external stimuli and the importance of conformational changes of proteins leading to pathogenic states has been well documented. Especially under conditions that destabilize the native state, proteins can aggregate into characteristic fibrillar assemblies, known as amyloid fibrils. These beta-sheet rich protein assemblies have distinctively different conformations compared to that of the native state. The misfolded prion protein is even self-propagating (infectious), a property which is entirely encoded within the misfolded conformation.

Chronic human diseases seriously affect the healthcare system. It is well recognized that rapid and accurate diagnostic tools are necessary to afford early intervention and therapy. Only symptomatic therapy is available, like in Alzheimer's disease for example, and these have limited therapeutic efficacy. Presently there are no antemortem molecular diagnostic tests of Alzheimer's disease or transmissible spongiform encephalopathies (TSEs), and the clinical diagnostics that are performed require that disease progression is severe. Further, there are no efficient treatments available yet, and immunotherapy in for example Alzheimer's disease holds great promise. The lack of reliable methods to capture misfolded proteins, monitoring both treatment and disease progression is however a severe shortcoming in treatment of most protein misfolding related diseases.

The affinity between misfolded proteins in amyloid plaques, amyloid fibrils and amyloid like fibrils, and conjugated molecules compromised of repeating units of thiophene, ethylenedioxythiophene (EDOT), benzothiadizole, fluorene, and phenyl in homo and hetero oligomers and polymers with ionic or polar sidechains has been demonstrated in several in vitro studies. The interaction between amyloid like fibrils of insulin and anionic, zwitterionic and cationic poly- and oligo thiophenes was shown by [WO2005/109005]. Several of the mentioned oligomers and polymers have been shown to bind to amyloid, aβ and PrP deposits in histological sections [WO2007/091973]. An anionic, more specifically an alkoxysulfonate derivative, polymer of EDOT showed high affinity for amyloid like fibrils [Hamedi, M. et al.;. Nano Lett.; (2008); 8, 1736-1740]. Moreover a susbtituted polyfluorene and an alternating polyfluorene with a polyethylene oxide were demonstrated to strongly associate with amyloid like fibrils in vitro [Tanaka, H. et al.; Nano Lett.; (2008) 8, 2858-2861].

SUMMARY OF THE INVENTION

In a first aspect, the present invention relates to a monodisperse compound of formula (I)

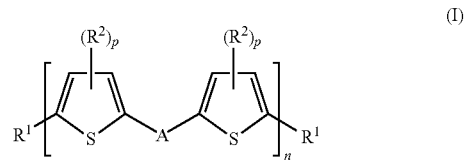

wherein
n is 1, 2, 3 or 4;
each p is independently 0, 1, 2;
each A is a moiety independently selected from thienylene, phenylene, fluorenylene, benzothienylene, ethylenedioxythienylene, benzothiadiazolylene and vinylene; which moiety is optionally substituted with 1 or 2 groups $R^3$; each $R^1$ is independently selected from H, phenyl and thienyl, optionally substituted with 1-3 groups $R^4$;

each $R^2$, $R^3$ and $R^4$ is independently selected from halogen, hydroxy, hydroxyalkyl, hydroxyalkoxy, hydroxyalkoxyalkyl, hydroxypolyoxyalkylene, alkoxy, alkoxyalkyl, polyoxyalkylene, carboxy, carboxyalkyl, carboxyalkoxy, carboxyalkoxyalkyl, carboxypolyoxyalkylene, alkoxycarbonyl, alkoxycarbonylalkyl, alkoxycarbonylalkoxy, alkoxycarbonylalkoxyalkyl, alkoxycarbonylpolyoxyalkylene, amino, alkylamino, dialkylamino, aminoalkyl, alkylaminoalkyl, dialkylaminoalkyl, aminoalkoxy, alkylaminoalkoxy, dialkylaminoalkoxy, aminopolyoxyalkylene, alkylaminopolyoxyalkylene, dialkylaminopolyoxyalkylene, aminoalkoxyalkyl, alkylaminoalkoxyalkyl, dialkylaminoalkoxyalkyl, (amino)(carboxy)alkyl, (alkylamino) (carboxy)alkyl, (dialkylamino) (carboxy) alkyl, (amino) (carboxy) alkoxy, (alkylamino)(carboxy)alkoxy, (dialkylamino)(carboxy)alkoxy, (amino)(carboxy)alkoxyalkyl, (alkylamino)(carboxy)alkoxyalkyl, (dialkylamino) (carboxy)alkoxyalkyl, (amino)(carboxy) polyoxyalkylene, (alkylamino)(carboxy)polyoxyalkylene, (dialkylamino)(carboxy)polyoxyalkylene, (alkoxycarbonyl) (amino) alkyl, (alkoxycarbonyl)(alkylamino)alkyl, (alkoxycarbonyl)(dialkylamino)alkyl, (alkoxycarbonyl) (amino)

alkoxy, (alkoxycarbonyl) (alkylamino) alkoxy, (alkoxycarbonyl) (dialkylamino) alkoxy, (alkoxycarbonyl) (amino) alkoxyalkyl, (alkoxycarbonyl) (alkylamino)alkoxyalkyl, (alkoxycarbonyl)(dialkylamino)alkoxyalkyl, (alkoxycarbonyl) (amino)polyoxyalkylene, (alkoxycabonyl) (alkylamino) polyoxyalkylene, (alkoxycabonyl)(dialkylamino)polyoxyalkylene, acylamino, acylaminoalkyl, acylaminoalkoxy, acylaminoalkoxyalkyl, acylaminopolyoxyalkylene, acylalkylamino, acylalkylaminoalkyl, acylalkylaminoalkoxy, acylalkylaminoalkoxyalkyl, acylalkylaminopolyoxyalkylene, hydrazinocarbonyl, hydrazinocarbonylalkyl, hydrazinocarbonylalkoxy, hydrazinocarbonylalkoxyalkyl, hydrazinocarbonylpolyoxyalkylene, nitro, nitroalkyl, nitroalkoxy, nitroalkoxyalkyl, nitropolyoxyalkylene, cyano, cyanoalkyl, cyanoalkoxy, cyanoalkoxyalkyl, cyanopolyoxyalkylene, sulfo, sulfoalkyl, sulfoalkoxy, sulfoalkoxyalkyl and sulfopolyoxyalkylene, or any two $R^2$ attached to the same thiophene ring taken together are alkylenedioxy, optionally substituted with sulfoalkyl, sulfoalkoxy, sulfoalkoxyalkyl or sulfopolyoxyalkylene, any $NH_2$ group may optionally be protected as a tert-butyl carbamate, benzyl carbamate or 9-fluorenylmethyl carbamate or substituted with a biotinyl moiety; and any alkyl or alkylene moiety is a C1-C6 alkyl or alkylene;

or a pharmaceutically acceptable salt thereof, for the treatment of a mammal suffering from a disease involving misfolded or aggregated forms of proteins.

In one aspect, the invention relates to a monodisperse novel compound of formula (II)

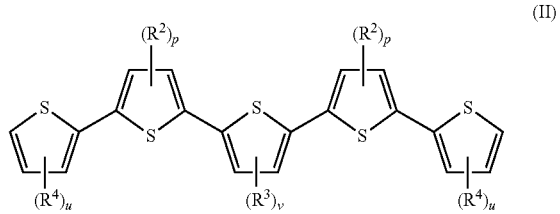

(II)

wherein each p is independently selected from 0, 1, 2;

v is 0, 1, 2;

each u is independently selected from 0, 1, 2, 3; with the proviso that not all p, v, u=O;

each $R^2$, $R^3$ and $R^4$ is independently selected from halogen, hydroxy, hydroxyalkyl, hydroxyalkoxy, hydroxyalkoxyalkyl, hydroxypolyoxyalkylene, alkoxy, alkoxyalkyl, polyoxyalkylene, carboxy, carboxyalkyl, carboxyalkoxy, carboxyalkoxyalkyl, carboxypolyoxyalkylene, alkoxycarbonyl, alkoxycarbonylalkyl, alkoxycarbonylalkoxy, alkoxycarbonylalkoxyalkyl, alkoxycarbonylpolyoxyalkylene, amino, alkylamino, dialkylamino, aminoalkyl, alkylaminoalkyl, dialkylaminoalkyl, aminoalkoxy, alkylaminoalkoxy, dialkylaminoalkoxy, aminopolyoxyalkylene, alkylaminopolyoxyalkylene, dialkylaminopolyoxyalkylene, aminoalkoxyalkyl, alkylaminoalkoxyalkyl, dialkylaminoalkoxyalkyl, (amino)(carboxy)alkyl, (alkylamino)(carboxy)alkyl, (dialkylamino)(carboxy) alkyl, (amino) (carboxy) alkoxy, (alkylamino)(carboxy)alkoxy, (dialkylamino)(carboxy)alkoxy, (amino)(carboxy)alkoxyalkyl, (alkylamino)(carboxy)alkoxyalkyl, (dialkylamino)(carboxy)alkoxyalkyl, (amino)(carboxy) polyoxyalkylene, (alkylamino) (carboxy)polyoxyalkylene, (dialkylamino) (carboxy)polyoxyalkylene, (alkoxycarbonyl) (amino) alkyl, (alkoxycarbonyl) (alkylamino) alkyl, (alkoxycarbonyl)(dialkylamino)alkyl, (alkoxycarbonyl)(amino) alkoxy, (alkoxycarbonyl) (alkylamino) alkoxy, (alkoxycarbonyl) (dialkylamino) alkoxy, (alkoxycarbonyl)(amino) alkoxyalkyl, (alkoxycarbonyl)(alkylamino)alkoxyalkyl, (alkoxycarbonyl)(dialkylamino)alkoxyalkyl, (alkoxycarbonyl) (amino)polyoxyalkylene, (alkoxycarbonyl) (alkylamino)polyoxyalkylene, (alkoxycarbonyl)(dialkylamino)polyoxyalkylene, acylamino, acylaminoalkyl, acylaminoalkoxy, acylaminoalkoxyalkyl, acylaminopolyoxyalkylene, acylalkylamino, acylalkylaminoalkyl, acylalkylaminoalkoxy, acylalkylaminoalkoxyalkyl, acylalkylaminopolyoxyalkylene, hydrazinocarbonyl, hydrazinocarbonylalkyl, hydrazinocarbonylalkoxy, hydrazinocarbonylalkoxyalkyl, hydrazinocarbonylpolyoxyalkylene, nitro, nitroalkyl, nitroalkoxy, nitroalkoxyalkyl, nitropolyoxyalkylene, cyano, cyanoalkyl, cyanoalkoxy, cyanoalkoxyalkyl, cyanopolyoxyalkylene, sulfo, sulfoalkyl, sulfoalkoxy, sulfoalkoxyalkyl and sulfopolyoxyalkylene, or any two $R^2$ attached to the same thiophene ring taken together are alkylenedioxy, optionally substituted with sulfoalkyl, sulfoalkoxy, sulfoalkoxyalkyl or sulfopolyoxyalkylene, any $NH_2$ group may optionally be protected as a tert-butyl carbamate, benzyl carbamate or 9-fluorenylmethyl carbamate or substituted with a biotinyl moiety; and any alkyl or alkylene moiety is a C1-C6 alkyl or alkylene; and pharmaceutically acceptable salts thereof. In still another aspect the invention relates to a compound according to formula (II) for use in therapy.

In a still further aspect the present invention relates to methods for therapy of diseases involving misfolded or aggregated forms of proteins, and the use of the inventive compounds in such methods.

In a further aspect, the invention comprises a mixture of at least two monodisperse compounds according to the invention.

In a further aspect, the invention relates to a pharmaceutical composition comprising at least one compound according to the first aspect and optionally pharmaceutically acceptable buffers, diluents, excipients and/or carriers.

The compounds according to the present invention should not be labelled for use in imaging methods.

(A) Effects of a treatment with p-FTAA on Aβ38, Aβ40 and Aβ42 in CSF: Graphs represent human Aβ38 (left), Aβ40 (mid), and Aβ42 (right) in CSF of hAPP Tg mice treated with vehicle or p-FTAA in 3 dosages. Data are represented as scattered dot plot with individual values and group mean with SD. Significant group differences are indicated with asterisks: * indicates $p<0.05$,  indicates $p<0.01$, * indicates $p<0.001$.

(B) Effects of a treatment with p-FTAA on Aβ38, Aβ40 and Aβ42 in brain homogenates: Graphs represent human Aβ38 (left), Aβ40 (mid), and Aβ42 (right) in 4 different brain homogenate fractions of hAPP Tg mice treated with vehicle or p-FTAA in 3 dosages. Data are represented as scattered dot plot with individual values and group mean with SD. Significant group differences are indicated with asterisks: * indicates $p<0.05$,  indicates $p<0.01$, * indicates $p<0.001$.

Figure 9:
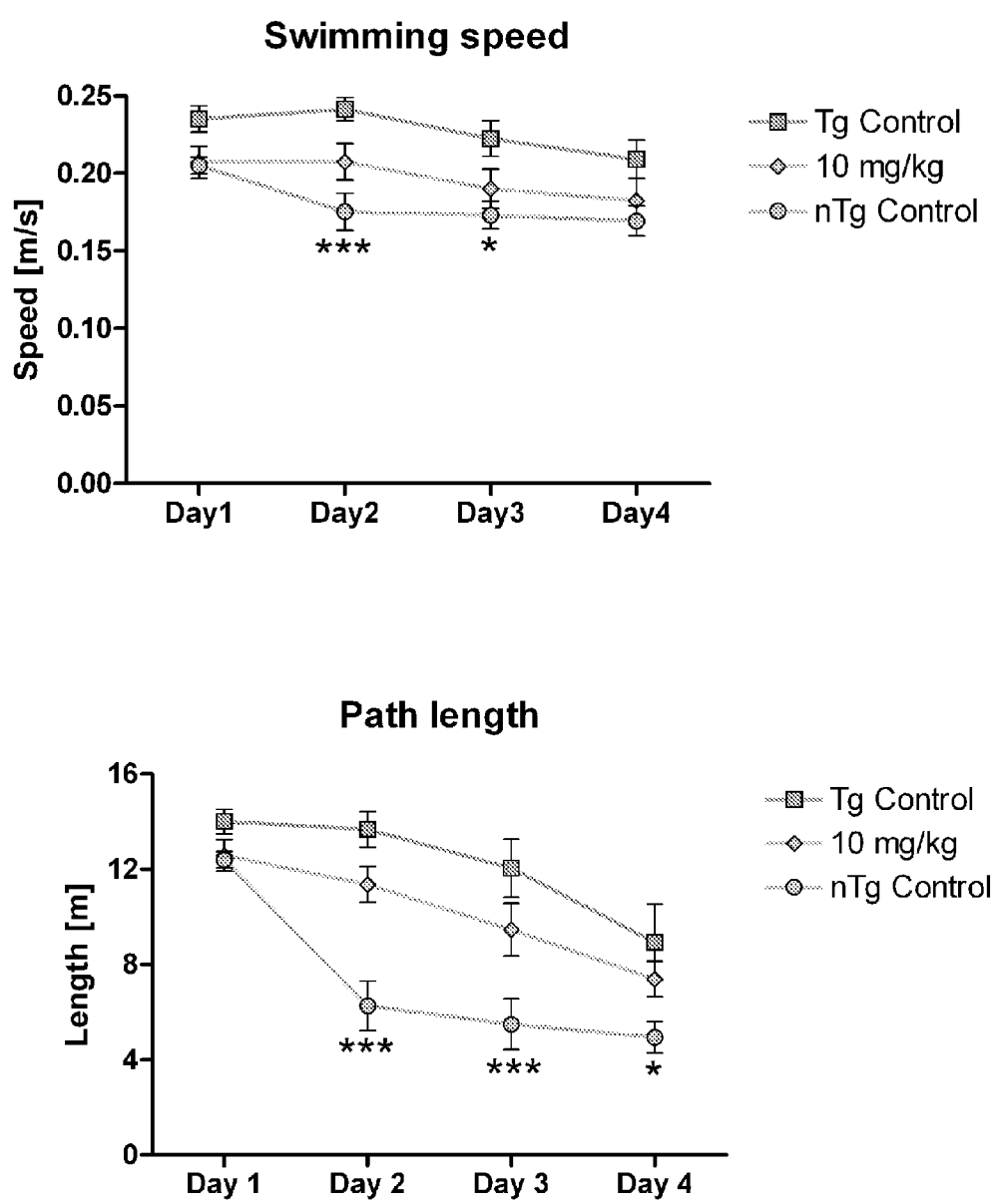

FIG. 9. Effects of a treatment with p-FTAA on behavior in the MWM: Graph represents swimming speed (top) and length of the swimming path (bottom) to reach the platform position in the MWM on Days 1-4 of Tg mice receiving vehicle (□), 10 mg/kg/day p-FTAA (◇) and nTg mice receiving vehicle (○). Data are displayed as group mean+SEM of all 3 trials per day. Significant group differences are indicated with asterisks: * indicates $p<0.05$,  $p<0.01$ and * $p<0.001$ for nTg Control vs Tg Control.

Figure 10:
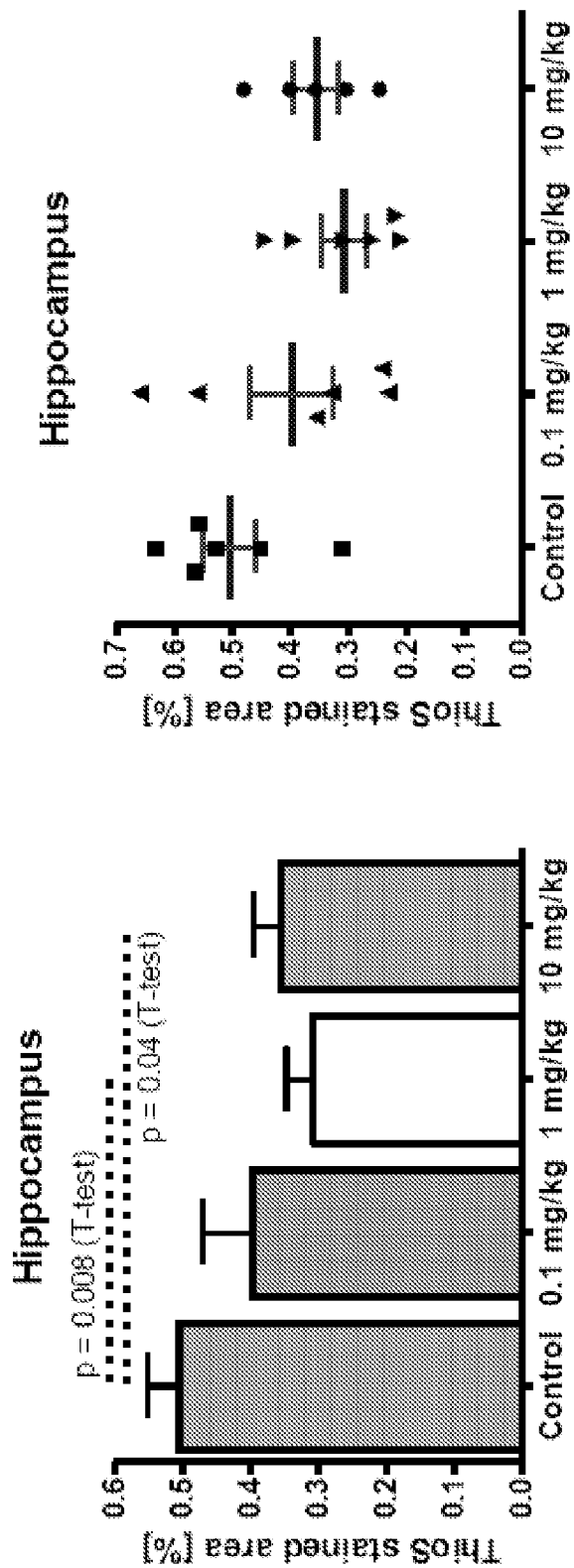

FIG. 10. Effects of a treatment with p-FTAA on the plaque area visualized by ThioflavinS staining: Graphs represent the ThioflavinS stained area in the cortex and the hippocampus of Tg mice receiving vehicle (N=6), 0.1 mg/kg/day p-FTAA (N=6), 1 mg/kg/day p-FTAA (N=6), 10 mg/kg/day p-FTAA (N=6). Data are represented as mean+SEM. The scattered bar indicates a significant difference in an unpaired two-tailed t-test. 1 mg/kg as well as 10 mg/kg p-FTAA treatment led to significantly lower plaque load in the hippocampus, while ThioflavinS positive plaque load was comparable among groups in the cortex.

Figure 11:
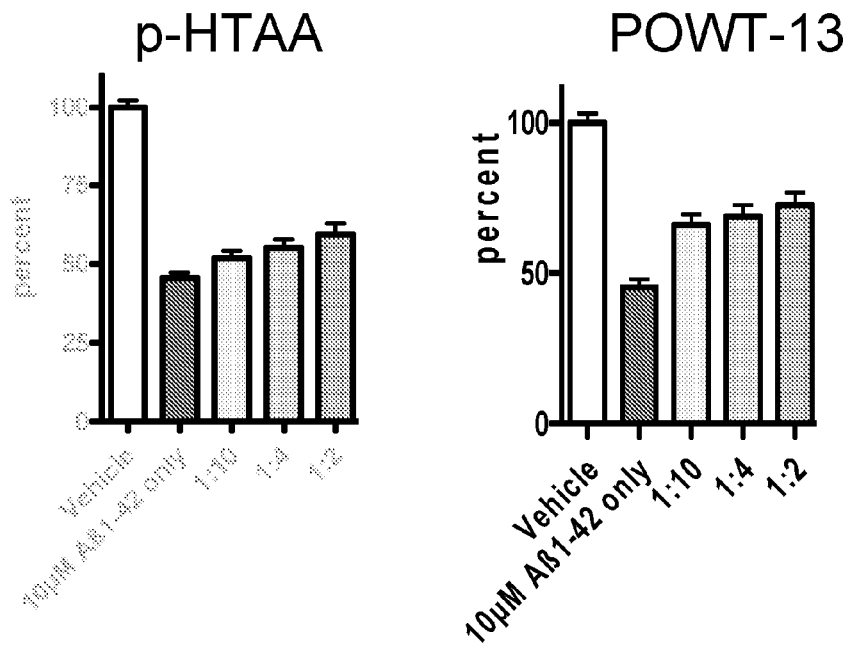

FIG. 11. Both p-HTAA and POWT-13 results in better viability compared to 10 μM Aβ1-42 alone. Stoichiometric ratios of T.I. to 10 μM Aβ1-42 is shown beneath the graph.

Figure 12:
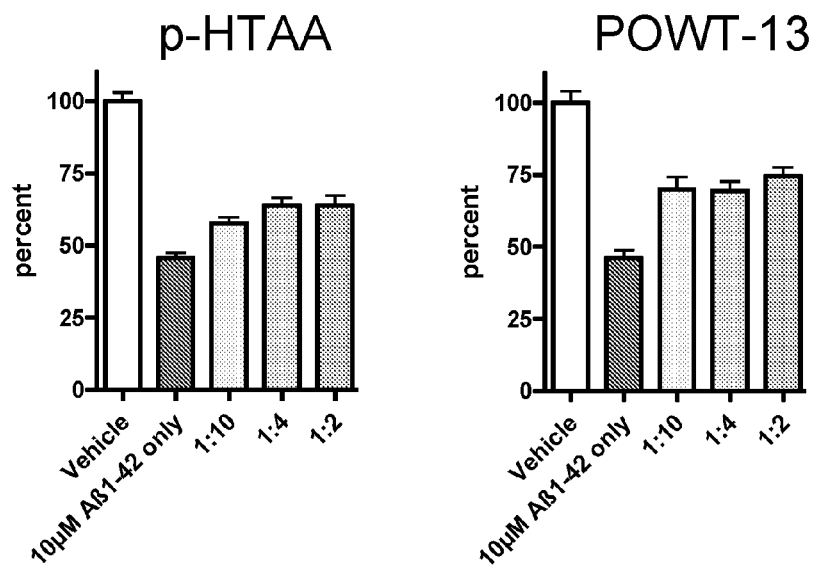

FIG. 12. Both p-HTAA and POWT-13 results in better viability compared to 10 μM Aβ1-42 alone. Stoichiometric ratios of T.I. to 10 μM Aβ1-42 is shown beneath the graph.

DETAILED DESCRIPTION OF THE INVENTION

Definitions

All words and abbreviations used in the present application shall be construed as having the meaning usually given to them in the relevant art, unless otherwise indicated. For clarity, some terms are however specifically defined below.

The term alkyl or alkylene moiety, as used herein, is a C1-C6 alkyl or alkylene moiety, e.g. a C1-C4 alkyl or alkylene moiety and is intended to encompass also the alkyl or alkylene portion of any functional group, e.g. an alkoxy, alkylamino or carboxypolyoxyalkylene group. Thus, for example, any alkyl in an alkoxy or alkylamino group according to the invention is a C1-C6 alkyl group, e.g. a C1-C4 alkyl group.

Also, any alkyl or alkylene group according to the invention may be branched or unbranched.

The term "alkyl" includes the monoradical derived from a branched or unbranched C1-C6 alkane, or C1-C4 alkane. Examples of an alkyl group are methyl ($CH_3$—), ethyl ($CH_3CH_2$—), propyl (—$CH_2CH_2CH_3$—) and isopropyl (($CH_3)_2CH$—).

The term "alkylene" includes the diradical derived from a branched or unbranched C1-C6 alkane, or C1-C4 alkane. Examples of an alkylene group are methylene (—$CH_2$—), ethylene (—$CH_2CH_2$—), propylene (—$CH_2CH_2CH_2$-) and isopropylene (—$CH(CH_3)CH_2$—).

The terms "thienylene", "phenylene", "fluorenylene", "benzothienylene", "ethylenedioxythienylene", "benzothiadiazolylene", "vinylene" include diradicals derived from thiophene, benzene, fluorene, 3,4-ethylenedioxythiophene, 2-benzothiophene (or benzo[c]thiophene), 2,1,3-benzothiadiazole, and ethylene, respectively.

The terms "hydroxyalkyl", "hydroxyalkoxy" "hydroxyalkoxyalkyl" and "hydroxypolyoxyalkylene", include an alkyl, alkoxy, alkoxyalkyl and polyoxyalkylene radical, respectively, carrying a hydroxy function.

The term "alkoxy" includes a group R—O—, wherein R is alkyl.

The term "alkoxyalkyl" includes an alkyl radical carrying an alkoxy function.

The term "polyoxyalkylene" includes a group of the general formula RO—(R'O)n- wherein n is an integer from 1 to 6, e.g. from 1 to 4, or 1 or 2; R is an alkyl radical and each R' is an independently selected alkylene radical.

The terms "carboxyalkyl", "carboxyalkoxy", "carboxyalkoxyalkyl" and "carboxypolyoxyalkylene" include an alkyl, alkoxy, alkoxyalkyl and polyoxyalkylene radical, respectively, carrying a carboxy function.

The term "alkoxycarbonyl" includes a radical —COOR, viz. an alkyl ester of a carboxylic acid function.

The terms "alkoxycarbonylalkyl", "alkoxycarbonylalkoxy", "alkoxycarbonylalkoxyalkyl", "alkoxycarbonylpolyoxyalkylene" include an alkyl, alkoxy, alkoxyalkyl and polyoxyalkylene radical, respectively, carrying an alkoxycarbonyl function.

The term "alkylamino" includes —NHR wherein R is alkyl.

The term "dialkylamino" includes —NRR' wherein R and R' are independently selected alkyl groups.

The terms "aminoalkyl", "alkylaminoalkyl", and "dialkylaminoalkyl" include an alkyl radical carrying an amino, alkylamino or dialkylamino function, respectively.

The terms "aminoalkoxy", "alkylaminoalkoxy", and "dialkylaminoalkoxy" include an alkoxy radical carrying an amino, alkylamino or dialkylamino function, respectively.

The terms "aminoalkoxyalkyl", "alkylaminoalkoxyalkyl", and "dialkylaminoalkoxyalkyl" include an alkoxyalkyl radical carrying an amino, alkylamino or dialkylamino function, respectively.

The terms "aminopolyoxyalkylene", "alkylaminopolyoxyalkylene", and "dialkylaminopolyoxyalkylene", include a polyoxyalkylene radical carrying an amino, alkylamino or dialkylamino function, respectively.

The term "acylamino" includes a moiety —NH—C(O)-alkyl.

The terms "acylaminoalkyl", "acylaminoalkoxy", "acylaminoalkoxyalkyl" and "acylaminopolyoxyalkylene" include an alkyl, alkoxy, alkoxyalkyl and polyoxyalkylene radical, respectively, carrying an acylamino function.

The term "acylalkylamino" includes a moiety —NR—C(O)-alkyl wherein R is alkyl.

The terms "acylalkylaminoalkyl", "acylalkylaminoalkoxy", "acylalkylaminoalkoxyalkyl" and "acylalkylaminopolyoxyalkylene" include an alkyl, alkoxy, alkoxyalkyl and polyoxyalkylene radical, respectively, carrying an acylalkylamino function.

The term "hydrazinocarbonyl" includes a moiety a —C(O)NH—NH2.

The terms "hydrazinocarbonylalkyl", "hydrazinocarbonylalkoxy", "hydrazinocarbonylalkoxyalkyl" and "hydrazinocarbonylpolyoxyalkylene", include an alkyl, alkoxy, alkoxyalkyl and polyoxyalkylene radical, respectively, carrying a hydrazinocarbonyl function.

The terms "(amino)(carboxy)alkyl", "(amino)(carboxy)alkoxy", "(amino)(carboxy)alkoxyalkyl" and "(amino)(carboxy)polyoxyalkylene" include an alkyl, alkoxy, alkoxyalkyl and polyoxyalkylene radical, respectively, carrying a carboxy and an amino function, preferably attached to the same carbon atom.

The terms "(alkylamino)(carboxy)alkyl", "(alkylamino)(carboxy)alkoxy", "(alkylamino)(carboxy)alkoxyalkyl" and "(alkylamino)(carboxy)polyoxyalkylene", include an alkyl, alkoxy, alkoxyalkyl and polyoxyalkylene radical, respectively, carrying a carboxy and an alkylamino function, preferably attached to the same carbon atom.

The terms "(dialkylamino)(carboxy)alkyl", "(dialkylamino)(carboxy)alkoxy", "(dialkylamino)(carboxy)alkoxyalkyl" and "(dialkylamino)(carboxy)polyoxyalkylene", include an alkyl, alkoxy, alkoxyalkyl and polyoxyalkylene radical, respectively, carrying a carboxy and a dialkylamino function, preferably attached to the same carbon atom.

The terms "(alkoxycarbonyl)(amino)alkyl", "(alkoxycarbonyl)(amino)alkoxy", "(alkoxycarbonyl)(amino)alkoxyalkyl" and "(alkoxycarbonyl)(amino)polyoxyalkylene", include an alkyl, alkoxy, alkoxyalkyl and polyoxyalkylene radical, respectively, carrying an alkoxycarbonyl and an amino function, preferably attached to the same carbon atom.

The terms "(alkoxycarbonyl)(alkylamino)alkyl", "(alkoxycarbonyl) (alkylamino)alkoxy", "(alkoxycarbonyl)(alkylamino)alkoxyalkyl" and "(alkoxycarbonyl)(alkylamino)-polyoxyalkylene", include an alkyl, alkoxy, alkoxyalkyl and polyoxyalkylene radical, respectively, carrying an alkoxycarbonyl and an alkylamino function, preferably attached to the same carbon atom.

The terms "(alkoxycarbonyl)(dialkylamino)alky", "(alkoxycarbonyl) (dialkylamino)alkoxy", "alkoxycarbonyl) (dialkylamino)alkoxyalkyl" and "(alkoxycarbonyl)(dialkylamino)polyoxyalkylene", include an alkyl, alkoxy, alkoxyalkyl and "polyoxyalkylene" radical, respectively, carrying an alkoxycarbonyl and a dialkylamino function, preferably attached to the same carbon atom.

The terms "nitroalkyl", "nitroalkoxy", "nitroalkoxyalkyl", "nitropolyoxyalkylene" include an alkyl, alkoxy, alkoxyalkyl and polyoxyalkylene radical, respectively, carrying a nitro function.

The terms "cyanoalkyl", "cyanoalkoxy", "cyanoalkoxyalkyl", "cyanopolyoxyalkylene" include an alkyl, alkoxy, alkoxyalkyl and polyoxyalkylene radical, respectively, carrying a cyano function.

The terms "sulfoalkyl", "sulfoalkoxy", "sulfoalkoxyalkyl", "sulfopolyoxyalkylene" include an alkyl, alkoxy, alkoxyalkyl and polyoxyalkylene radical, respectively, carrying a sulfo function.

The term "monodisperse" as used herein should be interpreted, as commonly known to a person skilled in the art, as a very narrow size distribution, i.e. the polydispersity index (PDI) should be close to 1.

It should be noted that the invention includes the compounds described herein in all possible geometric or stereomeric forms. Within the scope of the invention are cis- and trans-isomers, R and S enantiomers, diastereomers, and racemic mixtures of the mentioned compounds.

New Medical Use

As mentioned herein above, in a first aspect the invention relates to a monodisperse compound of formula (I) or a pharmaceutically acceptable salt thereof, for the treatment of a mammal, especially a mammal such as a human suffering from a disease involving misfolded or aggregated forms of proteins.

The compounds of the invention can be regarded as oligomers or polymers of monomers. It has been suggested in the prior art to produce oligomers or polymers of some of the monomers forming the basis of the compounds according to the present invention. However, polymers are most often polydisperse due to the ease and low cost of manufacture of polydisperse polymers as compared to monodisperse compounds. The compounds according to the present invention find their primary use as pharmaceuticals and thus need to be well-defined. The compounds of the invention are thus monodisperse.

In some embodiments of the invention, n is from 1 to 4; e.g. from 1 to 3, such as 1 or 2; and each p is independently O-2; e.g. O or 1;

each A is a moiety independently selected from thienylene, phenylene, fluorenylene, benzothienylene, ethylenedioxythienylene, benzothiadiazolylene and vinylene; e.g. thienylene, phenylene, and ethylenedioxythienylene, wherein each A is optionally substituted with 1 or 2 groups $R^3$ as defined herein above; each $R^1$ is independently selected from H, phenyl and thienyl, e.g. H and thienyl; optionally substituted with 1-3 groups $R^4$; e.g. 1 or 2 groups, or 1 group $R^4$, as defined herein above.

In some embodiments of the invention, each A is unsubstituted.

When A is thienylene, ethylenedioxythienylene or benzothienylene it preferably is a 2,5-diradical:

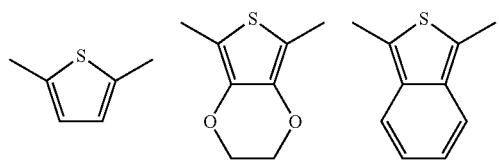

i.e. it is attached to the adjacent thiophene rings at the carbon atoms adjacent to its ring sulfur atom.

When A is phenylene it is preferably a 1,4-diradical:

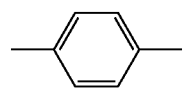

i.e. it is attached to the adjacent thiophene rings in para-position.

When A is benzothiadiazolylene it is preferably a 4,7-diradical:

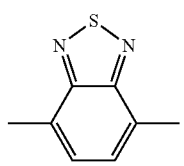

When A is fluorenyl it is preferably a 2,7-diradical:

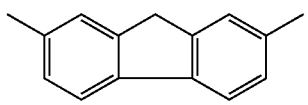

When A is vinylene, the thiophene rings preferably are in trans configuration:

In some embodiments, e.g. when n is 1, at least one of $R^1$ is not H; in some embodiments, both $R^1$ are not H.

In a compound according to either formula (I) as defined herein each $R^2$, $R^3$ and $R^4$ is independently selected from halogen, hydroxy, hydroxyalkyl, hydroxyalkoxy, hydroxyalkoxyalkyl, hydroxypolyoxyalkylene, alkoxy, alkoxyalkyl, polyoxyalkylene, carboxy, carboxyalkyl, carboxyalkoxy, carboxyalkoxyalkyl, carboxypolyoxyalkylene, alkoxycarbonyl, alkoxycarbonylalkyl, alkoxycarbonylalkoxy, alkoxycarbonylalkoxyalkyl, alkoxycarbonylpolyoxyalkylene, amino, alkylamino, dialkylamino, aminoalkyl, alkylaminoalkyl, dialkylaminoalkyl, aminoalkoxy, alkylaminoalkoxy, dialkylaminoalkoxy, aminopolyoxyalkylene, alkylaminopolyoxyalkylene, dialkylaminopolyoxyalkylene, aminoalkoxyalkyl, alkylaminoalkoxyalkyl, dialkylaminoalkoxyalkyl, (amino)(carboxy)alkyl, (alkylamino)(carboxy)alkyl, (dialkylamino)(carboxy) alkyl, (amino) (carboxy) alkoxy, (alkylamino)(carboxy)alkoxy, (dialkylamino)(carboxy)alkoxy, (amino)(carboxy)alkoxyalkyl, (alkylamino)(carboxy)alkoxyalkyl, (dialkylamino) (carboxy)alkoxyalkyl, (amino)(carboxy) polyoxyalkylene, (alkylamino)(carboxy)polyoxyalkylene, (dialkylamino) (carboxy)polyoxyalkylene, (alkoxycarbonyl) (amino)alkyl, (alkoxycarbonyl) (alkylamino)alkyl, (alkoxycarbonyl) (dialkylamino)alkyl, (alkoxycarbonyl)(amino) alkoxy, (alkoxycarbonyl)(alkylamino)alkoxy, (alkoxycarbonyl)(dialkylamino)alkoxy, (alkoxycarbonyl)(amino) alkoxyalkyl, (alkoxycarbonyl) (alkylamino)alkoxyalkyl, (alkoxycarbonyl)(dialkylamino)alkoxyalkyl, (alkoxycarbonyl)(amino)polyoxyalkylene, (alkoxycarbonyl) (alkylamino) polyoxyalkylene, (alkoxycarbonyl)(dialkylamino)polyoxyalkylene, acylamino, acylaminoalkyl, acylaminoalkoxy, acylaminoalkoxyalkyl, acylaminopolyoxyalkylene, acylalkylamino, acylalkylaminoalkyl, acylalkylaminoalkoxy, acylalkylaminoalkoxyalkyl, acylalkylaminopolyoxyalkylene, hydrazinocarbonyl, hydrazinocarbonylalkyl, hydrazinocarbonylalkoxy, hydrazinocarbonylalkoxyalkyl, hydrazinocarbonylpolyoxyalkylene, nitro, nitroalkyl, nitroalkoxy, nitroalkoxyalkyl, nitropolyoxyalkylene, cyano, cyanoalkyl, cyanoalkoxy, cyanoalkoxyalkyl, cyanopolyoxyalkylene, sulfo, sulfoalkyl, sulfoalkoxy, sulfoalkoxyalkyl and sulfopolyoxyalkylene, or any two $R^2$ attached to the same thiophene ring taken together are alkylenedioxy, optionally substituted with sulfoalkyl, sulfoalkoxy, sulfoalkoxyalkyl or sulfopolyoxyalkylene, and any $NH_2$ group may optionally be protected as a tert-butyl carbamate, benzyl carbamate or 9-fluorenylmethyl carbamate or substituted with a biotinyl moiety.

In some embodiments, each $R^2$, $R^3$ and $R^4$ is independently selected from halogen, alkoxy, alkoxyalkyl, polyoxyalkylene, carboxy, carboxyalkyl, carboxyalkoxy, carboxypolyoxyalkylene, alkoxycarbonyl, alkoxycarbonylalkyl, alkoxycarbonylalkoxy, alkoxycarbonylpolyoxyalkylene, amino, alkylamino, dialkylamino, aminoalkyl, alkylaminoalkyl, dialkylaminoalkyl, aminoalkoxy, alkylaminoalkoxy, dialkylaminoalkoxy, aminopolyoxyalkylene, alkylaminopolyoxyalkylene, dialkylaminopolyoxyalkylene, (amino)(carboxy)alkyl, (alkylamino)(carboxy)alkyl, (dialkylamino)(carboxy) alkyl, (amino)(carboxy)alkoxy, (alkylamino)(carboxy)alkoxy, (dialkylamino)(carboxy)alkoxy, (amino)(carboxy) polyoxyalkylene, (alkylamino)(carboxy)polyoxyalkylene, (dialkylamino) (carboxy)polyoxyalkylene, (alkoxycarbonyl) (amino)alkyl, (alkoxycarbonyl) (alkylamino) alkyl, (alkoxycarbonyl) (dialkylamino) alkyl, (alkoxycarbonyl) (amino) alkoxy, (alkoxycarbonyl) (alkylamino) alkoxy, (alkoxycarbonyl)(dialkylamino)alkoxy, (alkoxycarbonyl) (amino) polyoxyalkylene, (alkoxycarbonyl)(alkylamino)polyoxyalkylene, (alkoxycarbonyl)(dialkylamino)polyoxyalkylene, (alkoxycarbonyl)(alkylamino)alkoxy, (alkoxycarbonyl)(dialkylamino)alkoxy, and sulfoalkyl, sulfoalkoxyalkyl and sulfopolyoxyalkylene, or any two $R^2$ attached to the same thiophene ring taken together are alkylenedioxy, optionally substituted with sulfoalkyl, sulfoalkoxyalkyl or sulfopolyoxyalkylene, and any $NH_2$ may optionally be protected as a tert-butyl carbamate, benzyl carbamate or 9-fluorenylmethyl carbamate or substituted with a biotinyl moiety.

In some embodiments of the invention, each $R^2$, $R^3$ and $R^4$ is independently selected from halogen, alkoxy, carboxy, carboxyalkyl, alkoxycarbonylalkyl, aminoalkyl, diaminoalkoxy, (amino) (carboxy) alkoxyalkyl, (alkylamino) (carboxy) alkoxyalkyl, (dialkylamino) (carboxy)alkoxyalkyl, (alkoxycarbonyl)(amino)alkoxyalkyl, (alkoxycarbonyl)(alkylamino)alkoxyalkyl, (alkoxycarbonyl) (dialkylamino)alkoxyalkyl, and sulfoalkoxyalkyl or any two $R^2$ attached to the same thiophene ring taken together are alkylene dioxy, optionally substituted with sulfoalkyl, sulfoalkoxy, sulfoalkoxyalkyl or sulfopolyoxyalkylene, any primary amino group being optionally protected as a tert-butyl carbamate, benzyl carbamate or 9-fluorenylmethyl carbamate; and any alkyl or alkylene moiety is a C1-C6 alkyl or alkylene, e.g. C1-C4 alkyl or alkylene moiety.

In some embodiments, a compound of the invention may be represented by formula (I')

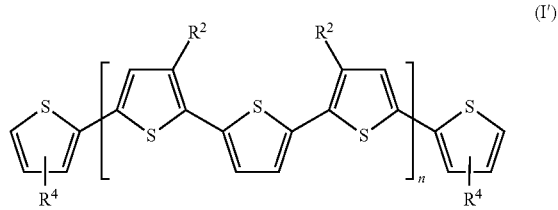

wherein
n is 1-4; e.g. 1-3, or 1 or 2; e.g. 1;

each $R^2$ is independently selected from carboxy, carboxyalkyl, alkoxycarbonylalkyl, aminoalkyl, (amino)(carboxy)alkoxyalkyl, (dialkylamino)(carboxy)alkoxyalkyl, (amino)(alkoxycarbonyl)alkoxyalkyl and (amino)(phenoxycarbonyl)alkoxyalkyl; and each $R^4$ is independently selected from hydrogen, halogen, carboxy, carboxyalkyl, alkoxycarbonylalkyl, aminoalkyl, (amino)(carboxy)alkoxyalkyl, (dialkylamino) (carboxy)alkoxyalkyl, (amino) (alkoxycarbonyl) alkoxyalkyl, (amino)(phenoxycarbonyl)alkoxyalkyl, acylamino, acylaminoalkyl, acylalkylamino and acylalkylaminoalkyl.

For example, each $R^2$ may be independently selected from carboxy, carboxymethyl, methoxycarbonylmethyl, aminomethyl, (amino) (carboxy)ethoxyethyl, (dimethylamino) (carboxy)ethoxyethyl, (amino)(methoxycarbonyl)ethoxyethyl and (amino)(phenoxycarbonyl)ethoxyethyl; and each $R^4$ may be independently selected from hydrogen, halogen, carboxy, carboxymethyl, methoxycarbonylmethyl, aminomethyl, (amino)(carboxy)ethoxyethyl, (dimethylamino)(carboxy)ethoxyethyl, (amino) (methoxycarbonyl) ethoxyethyl, (amino)(phenoxycarbonyl)ethoxyethyl.

In some embodiments, all groups $R^2$ are the same. In other embodiments, all groups $R^4$ are the same. In still other embodiments, all groups $R^2$ and $R^4$ are the same.

In some embodiments, the compound may be represented by formula (I")

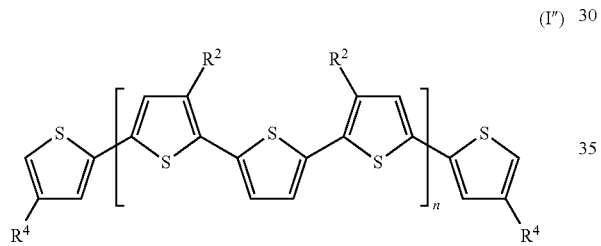

(I")

or by formula (I''')

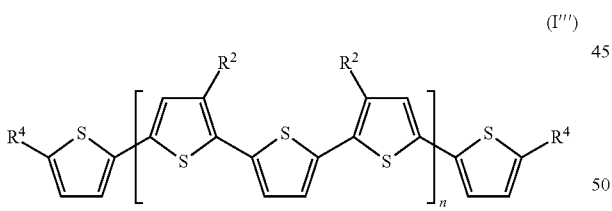

(I''')

or by formula (I'''')

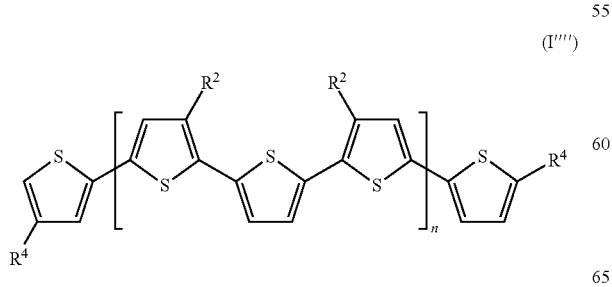

(I'''')

wherein n, $R^2$ and $R^4$ are as defined herein above.

Further examples of compounds are given below as compounds T1 to T18 where n=2-3, m=5-14 and k=2-5. All compounds can have one or several R-groups, wherein the R-groups in the respective positions are as defined above.

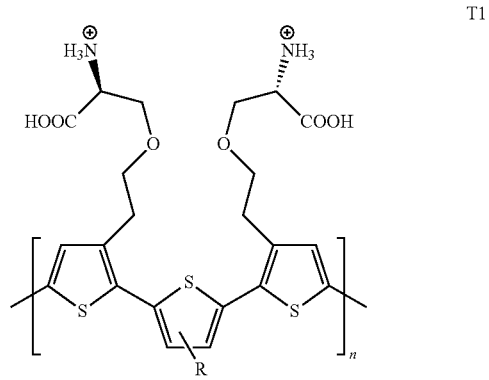

T1

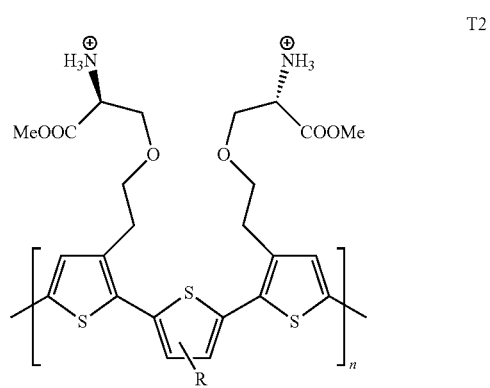

T2

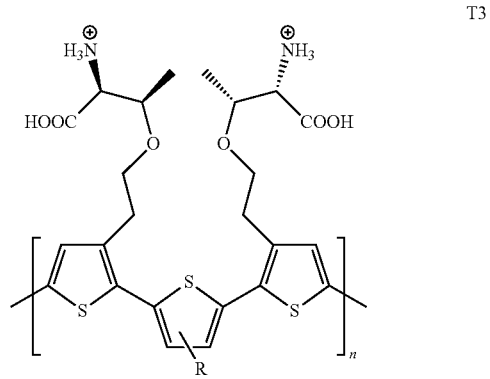

T3

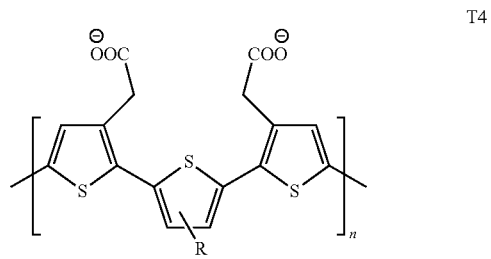

T4

T5
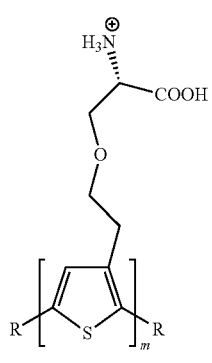
T6
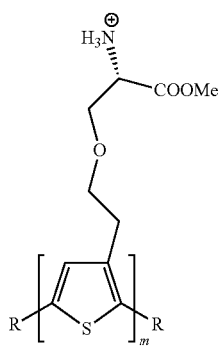
T7
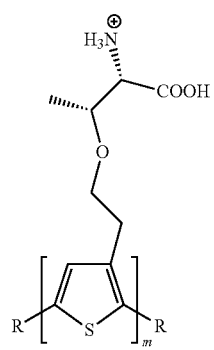
T8
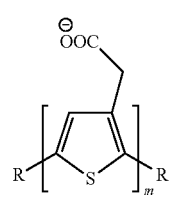
T9
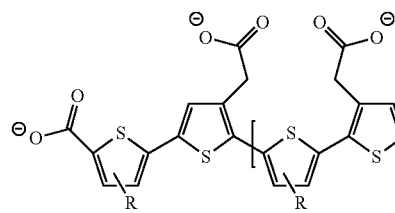
T10
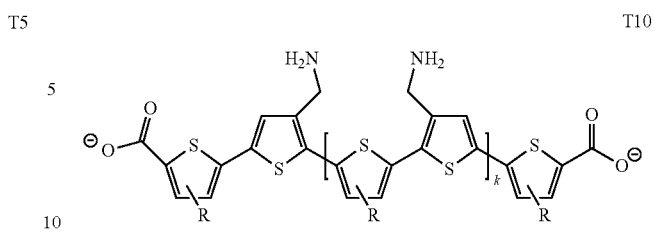
T11
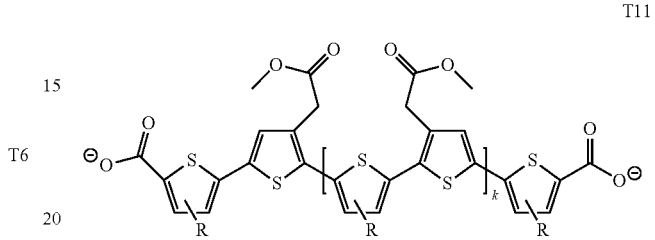
T12
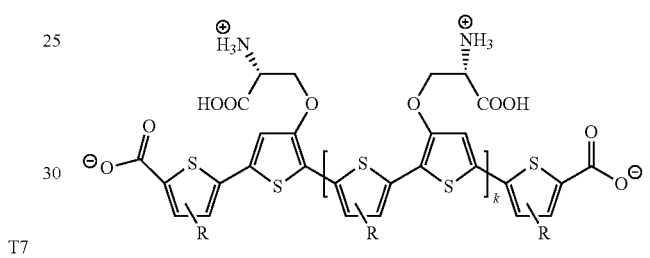
T13
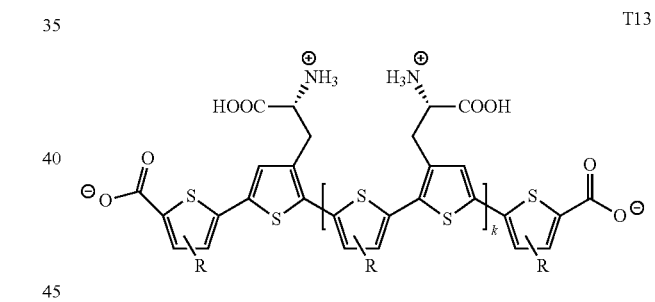
T14
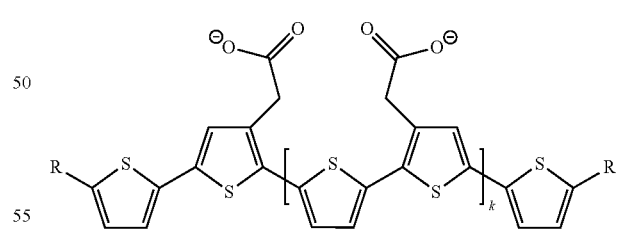
T15
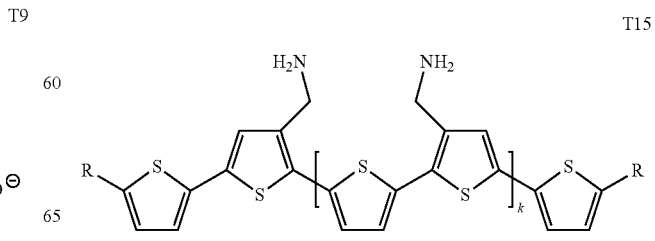

-continued

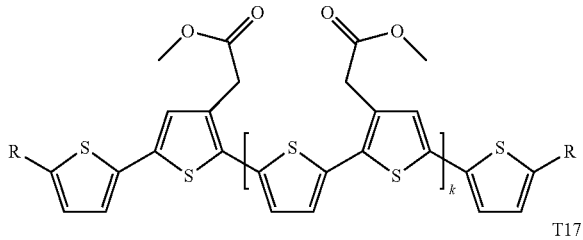

T16

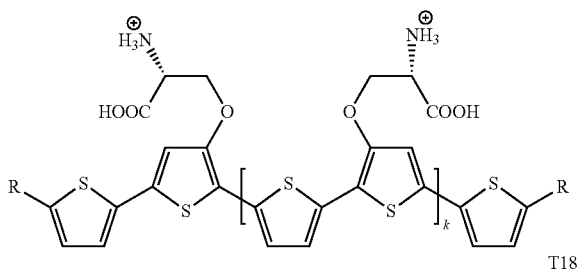

T17

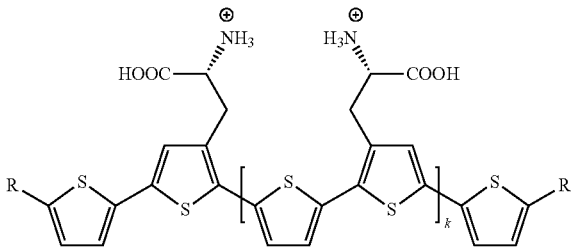

T18

Novel Compounds

In one aspect, the invention relates to a novel compound of formula (II)

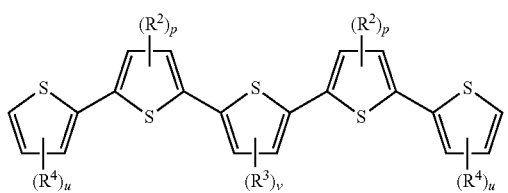

(II)

wherein each p is independently selected from 0-2; e.g. 0 or 1, and in particular is 1; each v is independently selected from 0-2; e.g. 0 or 1, and in particular is 0; each u is independently selected from 0-3; e.g. 0-2, and in particular is 0 or 1; with the proviso that not all p, v, u=0 each $R^2$, $R^3$ and $R^4$ is independently selected from halogen, hydroxy, hydroxyalkyl, hydroxyalkoxy, hydroxyalkoxyalkyl, hydroxypolyoxyalkylene, alkoxy, alkoxyalkyl, polyoxyalkylene, carboxy, carboxyalkyl, carboxyalkoxy, carboxyalkoxyalkyl, carboxypolyoxyalkylene, alkoxycarbonyl, alkoxycarbonylalkyl, alkoxycarbonylalkoxy, alkoxycarbonylalkoxyalkyl, alkoxycarbonylpolyoxyalkylene, amino, alkylamino, dialkylamino, aminoalkyl, alkylaminoalkyl, dialkylaminoalkyl, aminoalkoxy, alkylaminoalkoxy, dialkylaminoalkoxy, aminopolyoxyalkylene, alkylaminopolyoxyalkylene, dialkylaminopolyoxyalkylene, aminoalkoxyalkyl, alkylaminoalkoxyalkyl, dialkylaminoalkoxyalkyl, (amino)(carboxy) alkyl, (alkylamino) (carboxy) alkyl, (dialkylamino)(carboxy)alkyl, (amino)(carboxy)alkoxy, (alkylamino)(carboxy)alkoxy, (dialkylamino)(carboxy)alkoxy, (amino)(carboxy)alkoxyalkyl, (alkylamino)(carboxy)alkoxyalkyl, (dialkylamino) (carboxy)alkoxyalkyl, (amino)(carboxy) polyoxyalkylene, (alkylamino)(carboxy)polyoxyalkylene, (dialkylamino)(carboxy)polyoxyalkylene, (alkoxycarbonyl)(amino)alkyl, (alkoxycarbonyl) (alkylamino) alkyl, (alkoxycarbonyl) (dialkylamino) alkyl, (alkoxycarbonyl) (amino) alkoxy, (alkoxycarbonyl) (alkylamino)alkoxy, (alkoxycarbonyl)(dialkylamino)alkoxy, (alkoxycarbonyl) (amino)alkoxyalkyl, (alkoxycarbonyl) (alkylamino) alkoxyalkyl, (alkoxycarbonyl)(dialkylamino)alkoxyalkyl, (alkoxycarbonyl) (amino)polyoxyalkylene, (alkoxycarbonyl) (alkylamino)polyoxyalkylene, (alkoxycarbonyl)(dialkylamino)polyoxyalkylene, acylamino, acylaminoalkyl, acylaminoalkoxy, acylaminoalkoxyalkyl, acylaminopolyoxyalkylene, acylalkylamino, acylalkylaminoalkyl, acylalkylaminoalkoxy, acylalkylaminoalkoxyalkyl, acylalkylaminopolyoxyalkylene, hydrazinocarbonyl, hydrazinocarbonylalkyl, hydrazinocarbonylalkoxy, hydrazinocarbonylalkoxyalkyl, hydrazinocarbonylpolyoxyalkylene, nitro, nitroalkyl, nitroalkoxy, nitroalkoxyalkyl, nitropolyoxyalkylene, cyano, cyanoalkyl, cyanoalkoxy, cyanoalkoxyalkyl, cyanopolyoxyalkylene, sulfo, sulfoalkyl, sulfoalkoxy, sulfoalkoxyalkyl and sulfopolyoxyalkylene, or any two $R^2$ attached to the same thiophene ring taken together are alkylenedioxy, optionally substituted with sulfoalkyl, sulfoalkoxy, sulfoalkoxyalkyl or sulfopolyoxyalkylene;

any $NH_2$ group may optionally be protected as a tert-butyl carbamate, benzyl carbamate or 9-fluorenylmethyl carbamate or substituted with a biotinyl moiety;

wherein any alkyl or alkylene moiety is a C1-C6 alkyl or alkylene.

In some embodiments, each $R^2$, $R^3$ and $R^4$ is independently selected from halogen, carboxy, carboxyalkyl, carboxyalkoxy, carboxypolyoxyalkylene, alkoxycarbonyl, alkoxycarbonylalkyl, alkoxycarbonylalkoxy, alkoxycarbonylpolyoxyalkylene, amino, alkylamino, dialkylamino, aminoalkyl, alkylaminoalkyl, dialkylaminoalkyl, aminoalkoxy, alkylaminoalkoxy, dialkylaminoalkoxy, aminopolyoxyalkylene, alkylaminopolyoxyalkylene, dialkylaminopolyoxyalkylene, (amino)(carboxy)alkyl, (amino)(carboxy)alkoxy, any alkyl or alkylene moiety is a C1-C6 alkyl or alkylene, e.g. a C1-C4 alkyl or alkylene, more particularly a C1-C3 alkyl or alkylene, such as methyl or ethyl.

In some embodiments, each $R^2$, $R^3$ and $R^4$ is independently selected from halogen, carboxy, carboxyalkyl, carboxyalkoxy, carboxypolyoxyalkylene, alkoxycarbonyl, alkoxycarbonylalkyl, alkoxycarbonylalkoxy, alkoxycarbonylpolyoxyalkylene, amino, alkylamino, dialkylamino, aminoalkyl, alkylaminoalkyl, dialkylaminoalkyl, aminoalkoxy, alkylaminoalkoxy, dialkylaminoalkoxy, aminopolyoxyalkylene, alkylaminopolyoxyalkylene, dialkylaminopolyoxyalkylene.

In some embodiments, each $R^2$ is independently selected from halogen, carboxy, carboxyalkyl, alkoxycarbonyl, alkoxycarbonylalkyl, amino, alkylamino, dialkylamino, aminoalkyl, alkylaminoalkyl and dialkylaminoalkyl, e.g from carboxy, carboxyalkyl, alkoxycarbonyl, alkoxycarbonylalkyl, amino, aminoalkyl, or from carboxy, carboxyalkyl, alkoxycarbonylalkyl and aminoalkyl.

In some embodiments, each $R^4$ is independently selected from halogen, carboxy, carboxyalkyl, alkoxycarbonyl, alkoxycarbonylalkyl, amino, alkylamino, dialkylamino, aminoalkyl, alkylaminoalkyl and dialkylaminoalkyl, e.g from halogen, carboxy, carboxyalkyl, alkoxycarbonyl and alkoxycarbonylalkyl or from halogen, carboxy and carboxyalkyl, or halogen and carboxy.

For example each $R^2$, $R^3$ and $R^4$, in particular each $R^2$ and $R^4$ may be independently selected from fluoro, iodo, COOH, —CH$_2$COOH, —C$_2$H$_4$COOH, —CH$_2$COOCH$_3$, —CH$_2$NH$_2$, —C$_2$H$_4$NH$_2$, —OCH$_2$CH(NH$_2$)(COOH), and —CH$_2$CH(NH$_2$)(COOH).

In some embodiments, all groups $R^2$ are the same. In other embodiments, all groups $R^4$ are the same. In still other embodiments, all groups $R^2$ and $R^4$ are the same.

The central thienylene ring preferably is unsubstituted, i.e. v preferably is 0. The non-central thienylene or thienyl rings may be substituted or unsubstituted. However, at least one of the rings should preferably be substituted. In other words, at least one p, u and v preferably should be different from 0; and preferably at least one of p and u should be different from 0.

In some embodiments, the compound may be represented by formula (II')

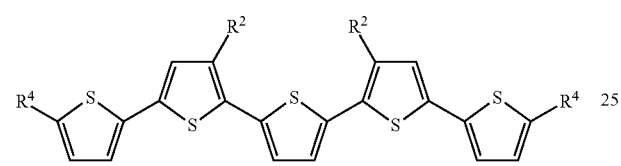
(II')

wherein $R^2$ and $R^4$ are as defined herein above;
or by formula (II")

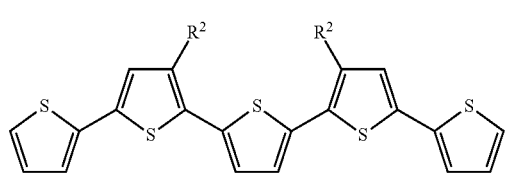
(II")

wherein $R^2$ is as defined herein above.

Some examples of compounds according to the present invention are the following:

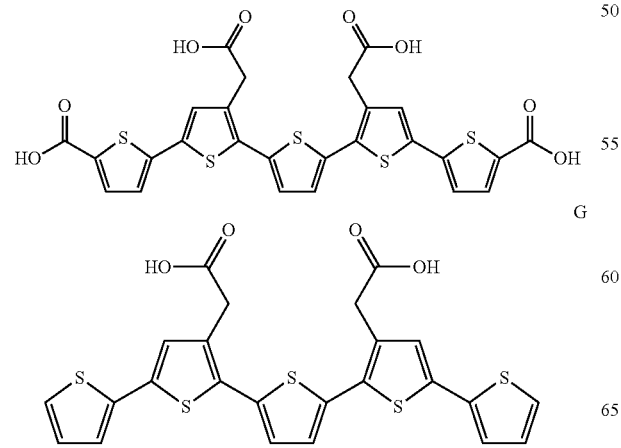
F

G

Other examples of compounds according to the invention are the following:

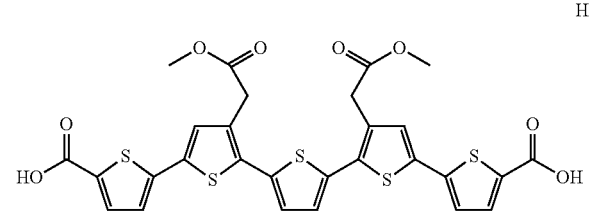
H

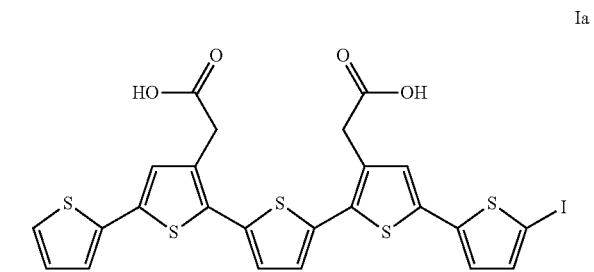
Ia

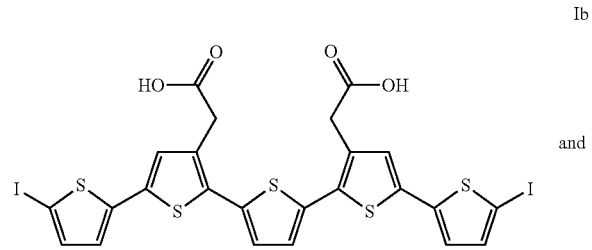
Ib and

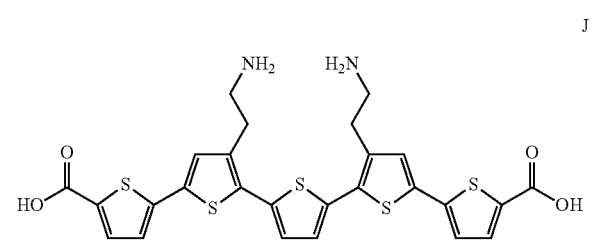
J

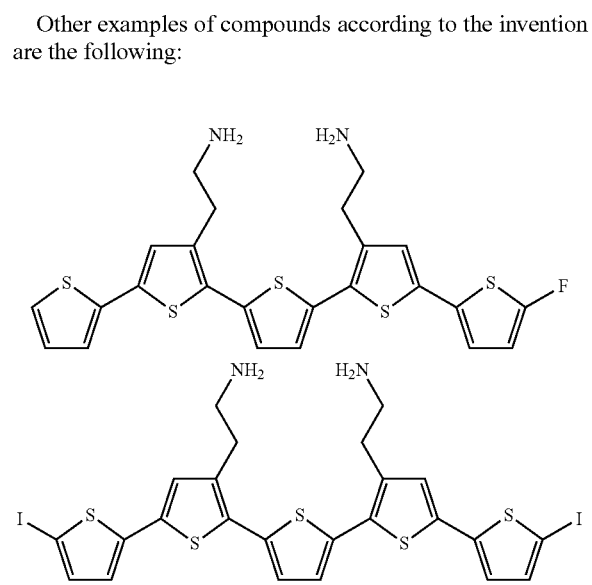

-continued
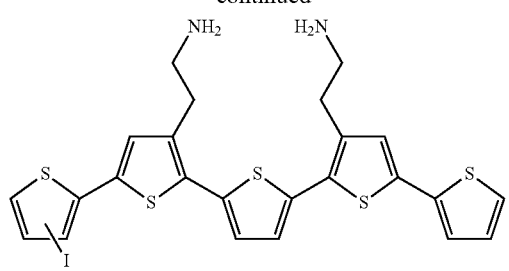
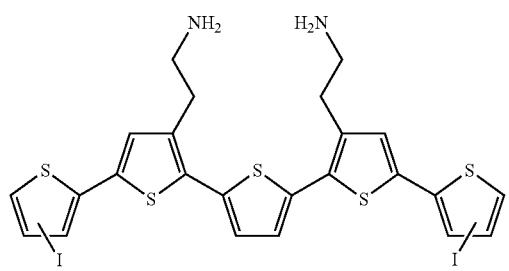
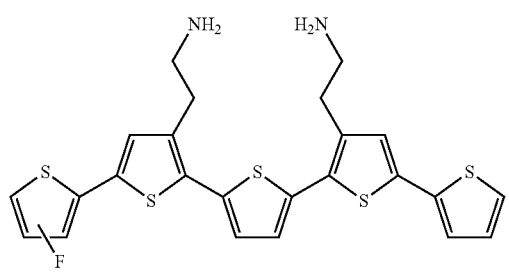
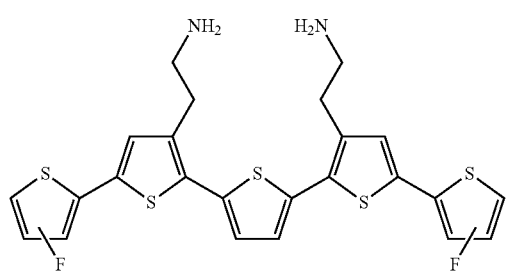
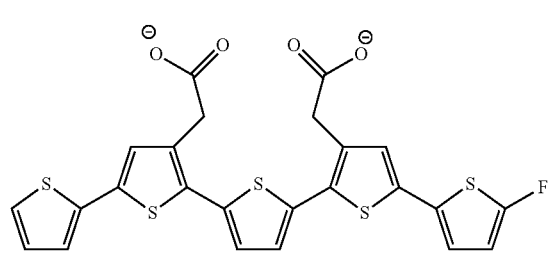
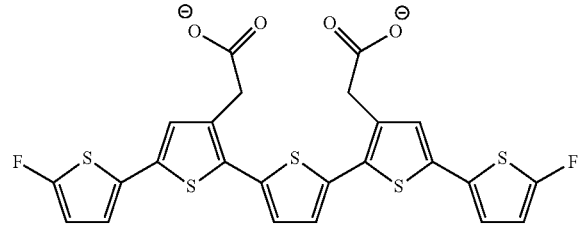
-continued
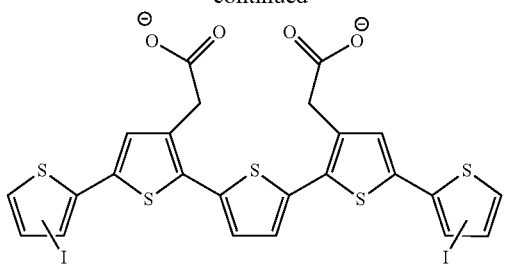
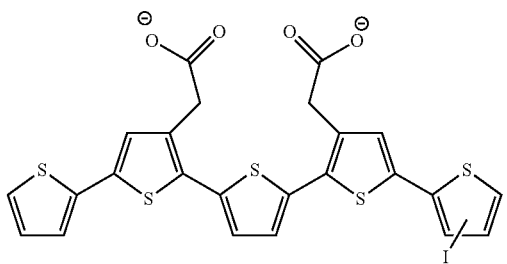
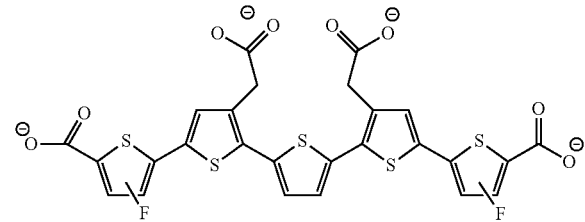
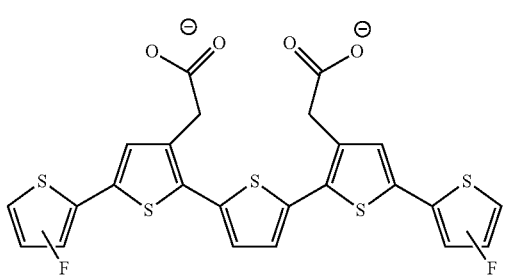
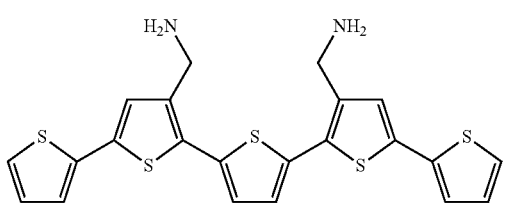
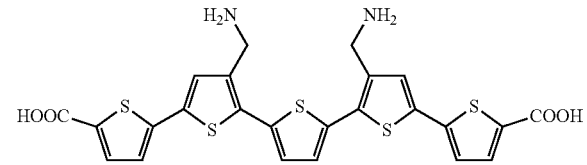
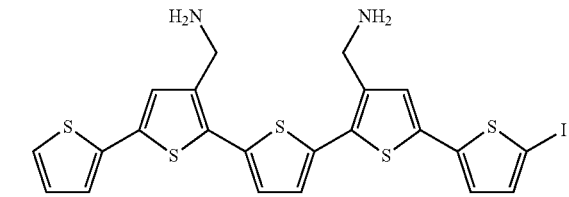

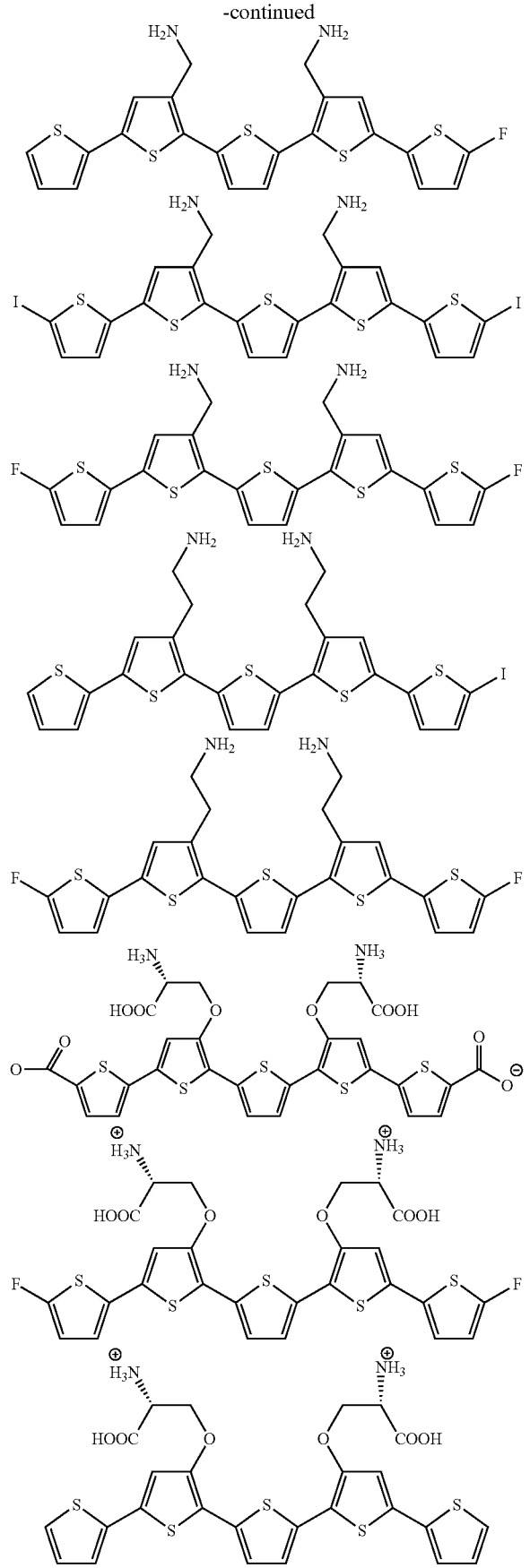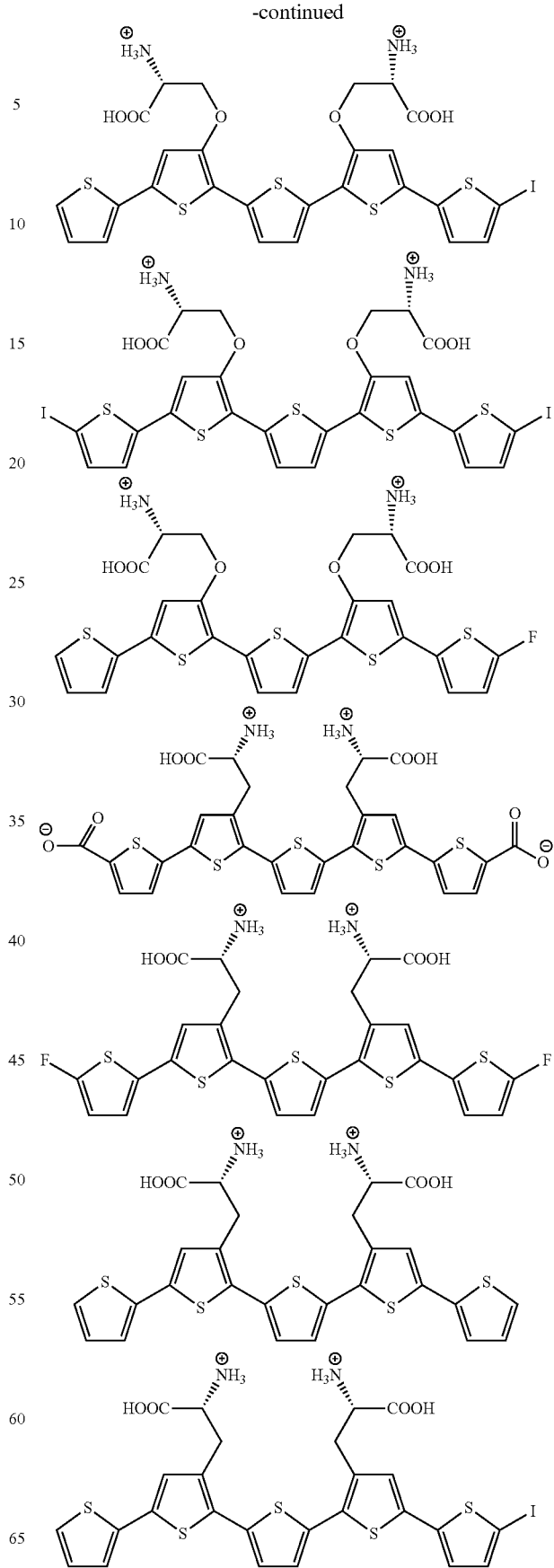

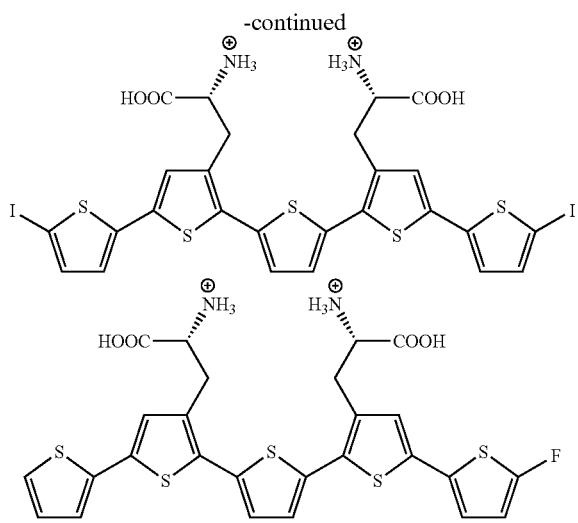

Methods of Preparation

The compounds of the present invention may be prepared by the person of ordinary skill in the art, in the light of the general description herein and the specific illustrating examples.

One example of a method of preparing a compound according to the present invention, is as follows:

In a first step, a compound according to formula (IV) (commercially available or synthesized e.g. by using Suzuki coupling), wherein A, $R^2$ and p are as defined herein above, is iodinated, to give a compound of formula (V):

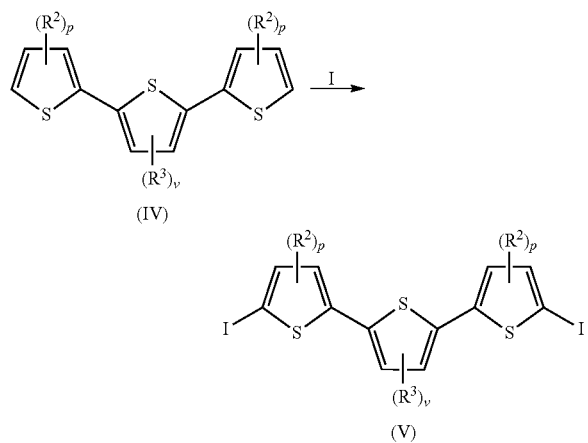

The compound of formula (V) then is reacted with 2-thiophene boronic acid under Suzuki coupling conditions, to give compound (II).

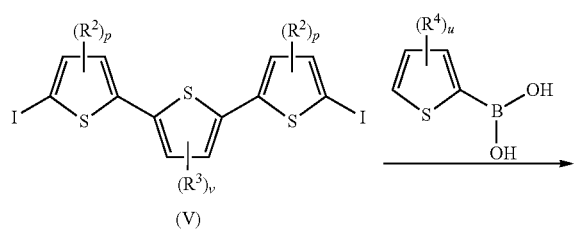

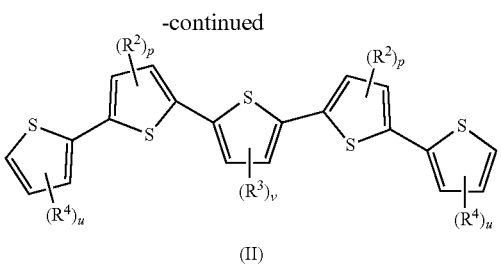

The inventive compounds also may be prepared by generally following the reaction sequence described for compound J in Example 4.

Generally, ring structures, i.e. thiophene, benzene, fluorene, benzothiophene, ethylenedioxythiophene, benzothiadiazole; and vinyl, serve as basic monomer units in the inventive compound. Substitutions of mentioned ring structures can be obtained through conventional chemistry, well known to one skilled in the art of organic synthesis and described in text books of organic synthesis, and exemplified in the synthesis examples below.

For preparation of polydisperse homo and copolymers disclosed in inventive compounds random oxidative polymerization of the mentioned ring structures using for example using iron(III)chloride can be performed. Such polymers can be size separated via well known separation methods including, but not limited to, dialysis and size exclusion chromatography.

To generate dimer, trimer, tetramer, pentamer etc. structures of mentioned ring structures several methods are known to those skilled in the art, here we mention the non-limiting examples of Suzuki and Stille coupling. Another well known method to generate polymers and oligomers of conjugated systems and some of the inventive compounds described herein is the so called Grignard Metathesis reaction, well described by McCullough. [Loewe, R. S.; Khersonsky, S. M.; McCullough, R. D. Adv. Mater. 1999, 11, 250-253.]

Stille coupling utilizes the coupling of an organotin compound with an $sp^2$-hybridized organic halide catalyzed by a palladium, exemplified by the schematic reaction from three ring units to a trimer-block:

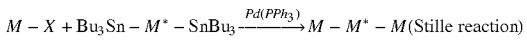

where $Bu_3Sn$ is tributylstannyl, M and M* symbolize arbitrary ring structure.

Suzuki coupling utilizes a reaction between an aryl- or vinyl-boronic acid or borate ester with a vinyl- or aryl-halide catalyzed by a palladium complex, exemplified by the schematic reaction:

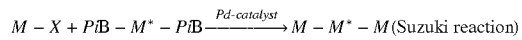

wherein PiB is a borate ester.

The reaction may also be carried out with pseudo-halides such as triflates.

The above mentioned examples describe the preparation of symmetric compounds. To prepare asymmetric compounds, e.g. a stoichiometric approach may be used, where the amount of reagent added is equimolar to the compound to be derivatized, if this compound has several reaction sites. As is well-known to the skilled person, from any mixture of symmetrical and/or asymmetrical compounds, the individual compounds may be separated by methods of chemical separation. Non-limiting examples of separation include flash column chromatography and distillation.

In certain aspects the inventive compounds may be used in form of "pharmaceutically acceptable salts", referring to derivatives of the disclosed compounds, where the described compounds are modified by making acid and base salts thereof. Non-limiting examples of pharmaceutically acceptable salts include mineral or organic salts of basic derivatives of the mentioned R-groups such as amines and organic or inorganic, e.g. alkali salts of acidic derivatives of the mentioned R-groups such as carboxylic acids. Conventional non-toxic salts and quaternary ammonium salts are included in pharmaceutically acceptable salts.

Pharmaceutically acceptable salts disclosed in the present invention may be prepared from the inventive compounds described herein that contain a basic or acidic entity by conventional chemical methods.

Diseases

The diseases to be treated with the compounds according to the present invention are diseases related to misfolded and aggregated proteins. Such diseases have also been termed proteopathies, (Walker and Levine, Curr Opin Investig Drugs. 2002 May; 3(5):782-7). Diseases featuring amyloid proteins are relevant examples for the description of diseases related to misfolded and aggregated proteins, where amyloidosis are known as a disease and may be inherited or acquired. Note that amyloidosis by default usually refers to AA amyloidosis, but any disease related to amyloid proteins, which presents amyloid deposition, is an amyloidosis. For example CJD, vCJD, Alzheimer's Disease and diabetes are almost never referred to as amyloidoses.

In this paragraph some examples of amyloidosis with relevance to the present invention are named. Primary amyloidosis includes mutations in lysozyme, transthyretin, apolipoprotein B, fibrinogen and AL amyloidosis (immunoglobulin light chains, as seen with multiple myeloma). Secondary amyloidosis includes AA amyloidosis (serum amyloid A protein, an acute-phase protein due to chronic inflammation) and Gelsolin amyloidosis (plasma gelsolin fragments). Familial or hereditary amyloidosis, are most commonly caused by mutations in the transthyretin protein, but in rare occurrences can also be caused by apolipoprotein A1, gelsolin, fibrinogen, and lysozyme mutations, primarily caused by genetics, believed to be autosomal dominant, high probability of passage to offspring, Appalachian type amyloidosis and Shar Pei fever for amyloidosis in Shar Peis. Examples of organ-specific amyloidosis are Diabetes mellitus type 2 (amylin, also known as IAPP), Alzheimer's disease (Aβ 39-42), Parkinson's disease (alpha-synuclein), Huntington's disease (huntingtin), Transmissible spongiform encephalopathies (prion protein, PrP), some examples are Creutzfeldt-Jakob disease (PrP in cerebrum), Kuru (diffuse PrP deposits in brain), Fatal Familial Insomnia (PrP in thalamus), Inclusion body myositis and Bovine spongiform encephalopathy (PrP in cerebrum of cows), Congophilic angiopathy (Amyloid beta). Cardiac amyloidosis includes congestive heart failure; some instances (PrP or transthyretin in heart). Another important example is the Iatrogenic conditions like insulin amyloidosis, believed to be caused by injection-administered insulin.

Some non-disease amyloids are native amyloids in organisms, Curli *E. coli* Protein (curlin), Yeast Prions [Sup35], Podospora Anserina Prion Het-s, Malarial coat protein, spider silk, Mammalian melanosomes (pMel), Tissue-type plasminogen activator (tPA) (a hemodynamic factor), Calcitonin and proteins and peptides engineered to make amyloid.

The prion diseases [e.g. bovine spongiform encephalopathy (BSE), and Creutzfeldt-Jakob disease (CJD)], are associated with the conformational conversion of the normal cellular prion protein, ($PrP^C$), to an infectious disease-associated isoform denoted $PrP^{Sc}$. The misfolded infectious form of the protein, $PrP^{sc}$ is the cause of a group of rare, fatal brain diseases, called prion diseases that affect humans and mammals. The prion diseases are also known as transmissible spongiform encephalopathies (TSE), and they include bovine spongiform encephalopathy (BSE, or "mad cow" disease) in cattle; scrapie in sheep; chronic wasting disease in deer and elk; and in humans [Creutzfeldt Jakob disease (CJD), Gerstmann-Sträussler-Scheinker disease (GSS), Kuru].

The compounds of the present invention are intended to be used for methods of therapy of the above diseases.

Use of Compounds in Therapy

The present invention also relates to the use of thiophene derivatives as novel therapeutic agents. The thiophene derivatives alter amyloid pathology upon administration to an organism, i.e. act as therapeutic agents. Conditions and diseases to be treated with the compounds according to the invention are conditions and diseases related to aggregation of misfolded proteins as discussed above by administrating a therapeutically effective amount of the compounds according to the invention to a subject in need thereof.

The thiophene derivatives of the present invention can be designed in order to cross the blood brain barrier and thereby have an effect on diseases that affect the brain, this include, but is not limited to, Abeta amyloid pathology in living organisms, i.e. influence Alzheimer's disease pathogenesis by acting as therapeutic agents.

The thiophene derivatives may be included in pharmaceutical preparations adapted for injection into the blood stream, to be taken orally, to be inhaled, to be taken up through the skin or mucus, for distribution into other body fluids, such as cerebrospinal fluid (CSF) or lymph.

Thus, in one aspect the present invention relates to a therapeutic composition, where at least one thiophene derivative is included, suitable for therapy of diseases related to misfolded protein species and a method of preparing and use of said therapeutic composition comprising administering a pharmaceutical composition containing at least one thiophene derivative variant, and optionally pharmaceutically acceptable excipients, buffers and/or carriers, to a subject in need thereof.

The inventive compounds may be administered by any means known to one of ordinary skill in the art. The present invention includes "pharmaceutically acceptable" compositions based on an amount of the inventive compound necessary for effective treatment of a patient together with one or more pharmaceutical carrier, such as additive and/or diluent. The inventive compounds may be formulated and administrated with other therapeutic agents. The formulation of the inventive compounds, may be determined by the means of administration. The formulation for administration of the inventive compounds may be solid, liquid or in aerosol form. Administration of the inventive compounds to an animal or human may be local or systemic accomplished parenterally, orally, by inhalation, rectally, nasally, buccally, vaginally or via an implanted reservoir. The term "parenteral" refers to administration outside the alimentary tract including subcutaneous, intravenous, intramuscular, intraarterial, intraspinal, intracranial, subdermal, intradermal by injection or infusion.

Carrier agents may be added to the pharmaceutical thiophene derivates compositions in order to achieve the desired distribution and acceptance in the living organism. Such agents include, but are not limited to, lipids, phospholipids, cellulose membranes, sugar coatings, hyaluronic acid, detergents, peptides, proteins, ions, salts, chelators and solvents.

The administered dose of the compounds should be a dose effective for treatment of the specific patient. The specific dose level of the inventive compound(s) will be dependent on several factors, including the activity and possible toxicity of the specific compounds used; the general health state, age, sex, body weight and diet of the subject or patient, the drug combination, the time and form of administration as well as the rate of excretion. The dose administered may typically be between 0.001 mg/kg/day to 50 mg/kg/day, preferably between 0.005 mg/kg/day to 10 mg/kg/day.

EXAMPLES

Therapeutic Effects of the Inventive Compounds

The present invention demonstrates novel anti-amyloid disease-modifying treatments based on the inventive compounds described herein. Current symptomatic treatments represent the opposite ends of the continuum of possible therapeutic outcomes in Alzheimer's disease and other diseases related to aggregated proteins. The inventive compounds can be used as anti-amyloid disease-modifying agents and, while not being bound by theory, it is suggested that these interrupt early pathological events by decreasing production of aggregated proteins or Aβ; by binding to existing aggregated proteins or Aβ; by inhibiting the formation of new aggregated protein or Aβ; or by increasing amyloid, aggregated proteins or Aβ clearance, thereby preventing all downstream pathological processes. One plausible mechanism, related to neurological diseases, is to use the inventive compounds to rescue viable neurons to achieve some degree of symptom relief or a full reversal of the disease. Other treatments may block events occurring downstream production of aggregated proteins or AP that affect some aspects of the disease.

Examples mentioned herein describes the first steps to show the therapeutic effects on misfolding diseases such as Alzheimer's of the inventive compounds (Scheme 2). Both in vitro and in vivo examples will further verify these effects.

In Vitro Fibrillation Inhibition Examples

An in vitro fibrillation of disease associated peptides and proteins, one non-limiting example is AP peptides, can be performed in presence of the inventive compounds and the effect of the molecular weight distribution of the aggregated species can be evaluated to demonstrate inhibitory effects. Molecular weight of aggregated species can be determined with gel electrophoresis, size exclusion chromatography and other methods well known in the art.

In Vivo Aβ Cell Assay Examples

The series of compounds of the present invention can be, but do not have to be, cell-permeable. As a model for Alzheimer's disease it is especially suitable to expose neural cells to aggregated species of Aβ peptides, where after cell responses and cell survival is studied. The therapeutic effects of the inventive compound can in this system be studied by exposing the neural cells to aggregated species of Aβ peptides and adding the inventive compounds simultaneously, before or after, whereupon protective effects of the compounds are evaluated. It can be demonstrated that one function, but not the only one, of the inventive compounds is to protect neurons from intracellular AbO toxicity by reducing the level of intraneuronal Ab oligomers (AbO) or by merely diminishing their toxicity.

AbO can induce toxicity when applied from outside the cells. One mode of toxicity is via the strong AbO binding to synapses, resulting in severe synaptic damage. Such binding activity may also be visualized using labeled AbO or a variant of the inventive compounds. The inventive compounds will be added before or after applying AbO to neuronal cultures, or other cell cultures, in order to demonstrate their activity. The inventive compounds will also be added at the same time, together with, the application of AbO to the cell cultures to further demonstrate their activity.

In Vivo Prion Assay Example

In vitro examples that are especially suitable for demonstrating therapeutic effects are cell culture or organotypic culture slide models of misfolding diseases. In the case of prion diseases the scrapie cell assay (SCA) has been known for at least five year as a model system, where prion infections can be studied via cell survival and quantification of prion protein. The therapeutic effects of the inventive compounds can be demonstrated through constant addition of these in the culture media or alternatively by a short exposure in a suitable media, whereupon cell survival and levels of prion protein would be measured. Another more in vivo like model system is the prion organotypic slice culture assay (POSCA) recently described by Aguzzi (Falsig and Aguzzi, Nat Prot, 2008, 3(4), 555-562). Brain culture slides are cultured up to 8 weeks and progression of prion infections can be monitored. In a similar fashion as with SCA, the culture slides can be constantly exposed to the inventive compounds or exposed in shorter doses, whereupon progression of the prion infection will be studies.

Demonstration of Efficacy In Vivo

We have demonstrated that an intravenous injection of the inventive compounds rapidly passed the blood brain barrier and permeated the brain producing a fluorescently highlighted amyloid plaques in AD mouse. There are several animal models of misfolding disease, for evaluating therapeutic effects of the inventive compounds transgenic mouse models are especially suitable. Non-limiting examples of mouse models are PS-APP and 5×FAD models. The present invention has demonstrated that the compounds of the inventionrecognize an amyloid conformation in AbO and in amyloid fibrils in transgenic mice. This binding can further be demonstrated in humanized mice and in humans. Being compatible with the human organism said compounds may be as therapeutics for man. The initial studies can include, but not limited to, a two week course of daily intraperitoneal injection of the inventive compounds in an AD-pathology model mice, humanized mice and later humans, in order to demonstrate the significant reduction of the quantity of amyloid lesions in the brain or in other parts of the body. No apparent toxicity should be observed. The reduction of the cerebral levels of protein or Ab aggregates by the inventive compounds might also be, but not necessarily, be confirmed by Western blot. Furhtermore behavioural changes, e.g. cognitive improvements, will be studied as a response of the exposure to the inventive compounds. The therapeutic use of known amyloid ligands, such as PIB and other derivatives of Congo red and thioflavins, is as far as the inventors of the present invention know restricted by limited ability for their synthetic modifications. The unique advantage of the inventive compounds series is that they are the first example of amyloid ligands derived from a thienyl library and that they can be oligomerized and polymerized to achieve further distinct properties. An oligomeric or polymeric structure can be of a great advantage when further modifications will be put on the core chemical structure. The inventive compound series contain a core structure with three plus two thienyl, or other groups as described in the present invention. These are chemical unities perfectly suitable for generating new libraries and to achieve the therapeutic effect related to diseases caused by aggregated proteins.

Example 1

Compound G (p-HTAA)

The trimeric building block (1 in scheme 1), synthesized with a previously reported protocol (Aslund A et al, Bioconjugate Chem., 2007, 18 (6), 1860-1868], was iodinated before it was coupled with 2-thiophene boronic acid under Suzuki coupling like conditions to give p-HTAA (3 in Scheme 1). 3 (0.200 g, 0.359 mmol) was further added to a solution of dioxane/NaOH (1 M, aq.) (1:1, 2 mL). After 1 h the solution was neutralized with HCl (1 M, aq.) and the precipitate was collected by centrifugation. The precipitate was washed with H2O to give the unsalted form of p-HTAA in quantitative yield (190 mg), which was converted to its corresponding sodium salt by dissolving it in H2O (3 mL) and NaOH (29 mg, 0.725 mmol) and freeze dried to afford the product p-HTAA (4, 0.205 g).

HRMS calcd for C24H16O4S5: [M+H]+: 528.9725; Found 528.9723

13C NMR (DMSO-D6) δ: 34.6, 124.5, 126.0, 127.2, 128.0, 128.5, 130.1, 132.7, 134.6, 134.7, 135.6, 171.5

1H-NMR (DMSO-D6) δ: 3.76 (s, 4H), 7.12 (dd, 2H, J=3.57 5.22 Hz), 7.28 (s, 2H), 7.30 (s, 2H), 7.35 (dd, 2H, J=1.10 3.57 Hz), 7.51 (dd, 2H, J=1.10 5.22 Hz)

Example 2

Compound H (p-FTAM)

The trimeric building block (1 in scheme 1), synthesized with a previously reported protocol (Aslund A et al, Bioconjugate Chem., 2007, 18 (6), 1860-1868 (2007)), was iodinated (2 in Scheme 1). The iodide (2, 0.068 g, 0.106 mmol), 5-(dihydroxyboryl)-2-thiophenecarboxylic acid (0.072 g, 0.419 mmol) and K2CO3 (0.090 g, 0.651 mmol) were dissolved in toluene/methanol (1:1, 5 mL) and argon bubbled for 10 minutes. After addition of PEPPSI™-IPr ([1,3-Bis(2,6-Diisopropylphenyl) imidazol-2-ylidene](3-chloropyridyl)-palladium(II) dichloride) (0.003 g, 0.004 mmol) the reaction vessel was subjected to microwave conditions (10 min., 80° C.). The mixture was diluted with HCl (1 M, aq.) and the red precipitate was collected and dissolved in boiling dioxane, filtered on celite and precipitated by addition of H2O to give p-FTAM (5) as a red powder in 85% yield (0.090 g).

HRMS calcd for C28H19O8S5: [M−H]− 642.9684; Found 642.9645

13C NMR (DMSO-D6) δ: 34.1, 52.1, 125.1, 127.8, 129.7, 132.2, 132.3, 133.2, 133.7, 134.3, 134.5, 141.7, 162.5, 170.4

Example 3

Compound F (p-FTAA)

Compound H (p-FTAM, 0.200 g, 0.310 mmol, 5 in Scheme 1) was added to a solution of dioxane/NaOH (1 M, aq.) (1:1, 2 mL). After 1 h the solution was neutralized with HCl (1 M, aq.) and the precipitate was collected by centrifugation. The precipitate was washed with H2O to give the unsalted form of p-FTAA in quantitive yields (191 mg) which were converted to its corresponding sodium salt by dissolving it in H2O (3 mL) and NaOH (29 mg, 0.720 mmol) and freeze drying it to afford the product p-FTAA (6, 0.207 g).

HRMS calcd for C26H15O8S5: [M+H]-614.9371; Found 614.9422

13C NMR (D20, 45° C.) δ: 38.4, 124.4, 126.6, 129.1, 131.9, 132.0, 134.4, 134.7, 135.5, 139.6, 140.9, 169.9, 179.4
1H-NMR (DMSO-D6) δ: 3.76 (s, 4H), 7.32 (s, 2H), 7.38 (d, 2H, J=4.10 Hz), 7.45 (s, 2H), 7.66 (d, 2H, J=4.10 Hz)

Scheme 1.

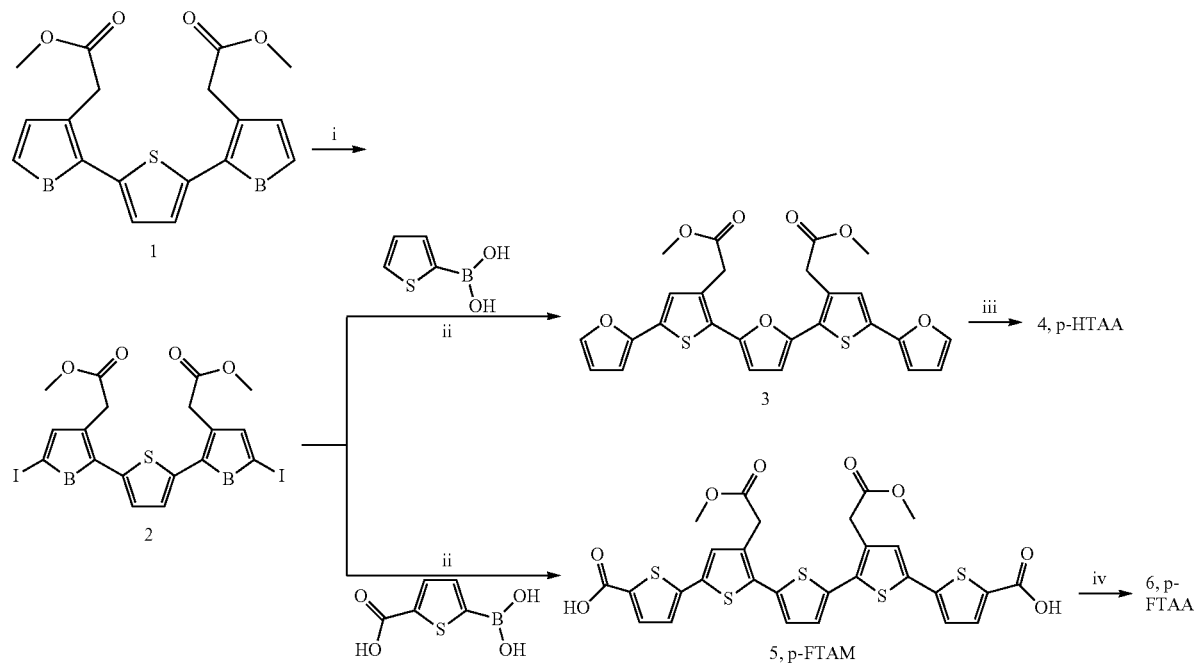

Example 4

Compound J (p-PAMT)

3-Thiophene-ethanol was dissolved and stirred in CHCl₃/HOAc (1:1) at 0° C. and N-Iodo-succinimide was added portion wise for 20 minutes. The reaction was quenched with 20 mL water after 19 hours and the organic layer was washed with 2*50 mL saturated $Na_2S_2O_3$-solution, 2*50 mL water, dried, filtered, concentrated, and purified by flash column chromatography (Toluene/EtOAc 18:1) to give 1 (Scheme 2). 1 was dissolved in CHCl₃/Pyridin (7:1) at 0° C. and p-toluenesulfonylchloride was added for 5 minutes. After 19 hours the reaction was quenched with 15 mL water and diluted with 40 mL diethyleter. The organic layer was washed with 2*40 mL 2M HCl, 2*50 mL saturated NaHCO₃-solution, 2*50 mL water, dried, filtered, concentrated, and purified by flash column chromatography (Toluene) to give 2. 2, Di-tert-iminodicarboxylate, and $K_2CO_3$ were dissolved in DMF (dry) and heated in an oil bath at 75° C. After 4 hours, EtOAc (50 mL) and water (30 mL) were added. The organic layer was washed with 2*20 mL 2M HCl, 2*15 mL water, 2*15 mL brine, dried, filtered, concentrated, and purified by flash column chromatography (Toluene) to give 3. 3, Thiophene-diboronic-ester and $K_2CO_3$ was dissolved in a degassed solution of Toluene/MeOH (1:1) at room temperature and treated under argon. After 10 minutes PEPPSI™-IPr was added and the reaction was run in a microwave oven at 80° C. for 10 minutes. The solution was diluted with toluene (20 mL), washed with 2M HCl (10 mL), water (15 mL), dried, filtered, concentrated, and purified by flash column chromatography (Toluene/EtOAc 18:1) to give 4. 4 was dissolved in CHCl₃ (15 mL) at 0° and first HOAc (15 mL) and finally N-Iodosuccinimide was added. After 17 hours the reaction was quenched with water (10 mL) and the organic layer was washed with 2*50 mL saturated $Na_2S_2O_3$— solution, 2*50 mL water, dried, filtered, concentrated, and purified by flash column chromatography (Toluene/EtOAc 18:1) to give 5. 5, 2-Carboxythiophene-5-boronic acid, and $K_2CO_3$ was dissolved in a degassed solution of T/MeOH (1:1) at room temperature and treated under argon. After 10 minutes PEPPSI was added and the reaction was run in a microwave oven at 80° C. for 10 minutes. The solution was treated with 1M HCl (10 mL) and a red precipitation was obtained. The red flakes i.e. the crude product, were collected and purified by flash column chromatography (EtOAc/MeOH 10:1>>EtOAc/MeOH 10:1+1% HOAc) to give 6. 6 was dissolved in CHCl₃ at room temperature and then TFA was added. The solution was stirred at room temperature for 3 hours. After 3 hours the reaction was quenched with MeOH and evaporated to give the final product as red flakes (7 in Scheme 2).

MALDI-TOF MS cald: 586.65. Found: 586.79

Scheme 2

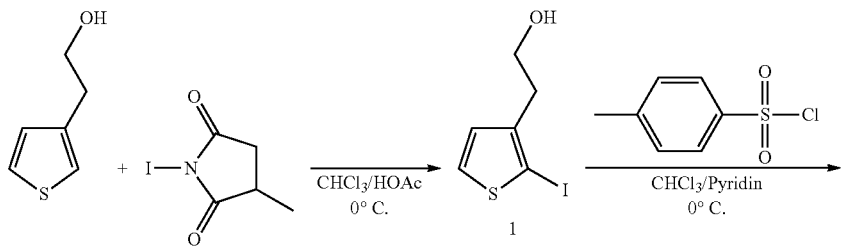

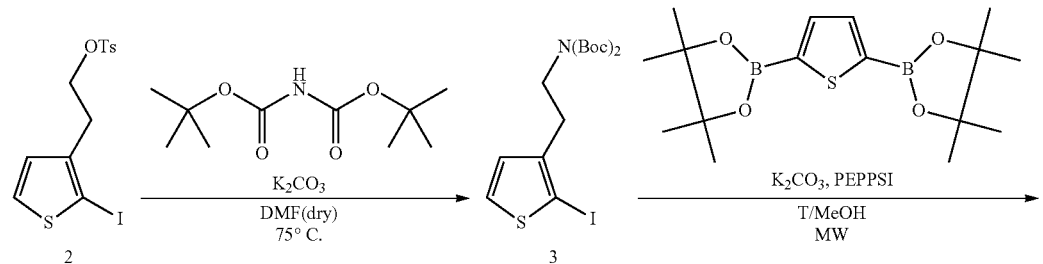

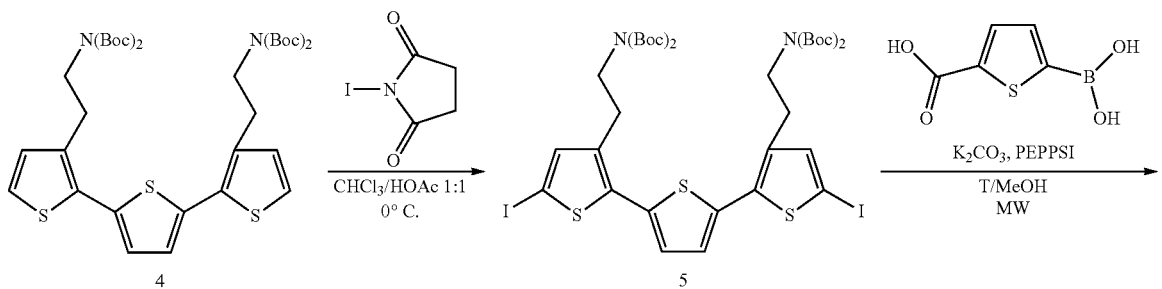

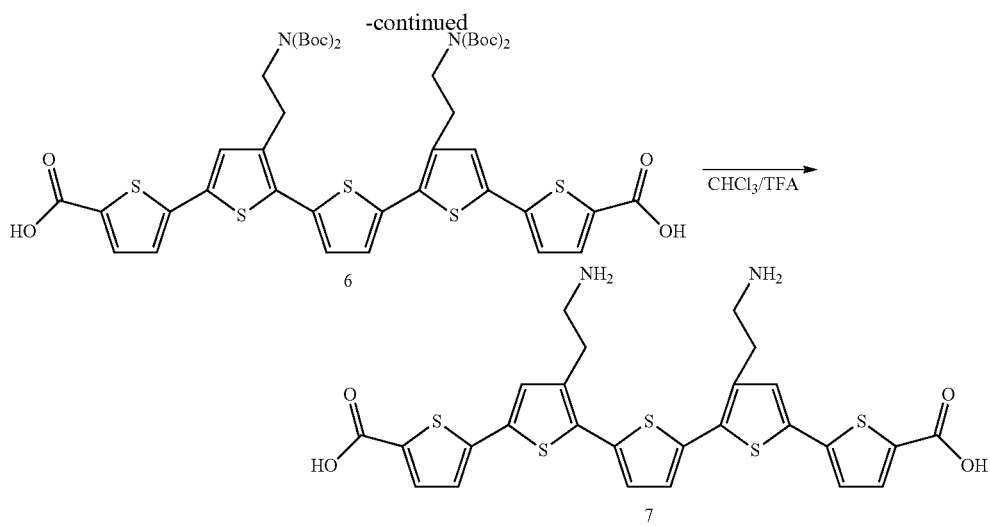

Example 5

Compounds Ia and Ib 1 (Scheme 3) was dissolved in CHCl₃ at room temperature. HOAc was added in a 1:1 ratio and the mixture cooled to 0° C., whereupon N-Iodo-succinimide was added. The reaction was quenched with 3 mL water after 19 hours in darkness and the organic phase was washed with 2*30 mL saturated Na₂S₂O₃-solution, 2*30 mL water, dried, filtered, concentrated and purified flash column chromatography (Toluene/EtOAc 18:1) to give a mixture of 2 and 3 (scheme 5). The mixture 2 and 3 was dissolved in dioxane at room temperature, 1 M NaOH was added and after 7 hours the reaction was neutralized with 1 M HCl. The product compound Ia and Ib (4 and 5) was collected as a precipitate by centrifugation.

¹H-NMR (DMSO-d6, 300 MHz): 63.49 (s, 4H), 7.0 (s, 2H), 7.35 (d, 2H J=4.8 Hz), 7.45 (d, 2H, J=3.6 Hz), 7.67 (d, 1H, J=5.1 Hz), 7.75 (s, 2H).

MALDI-TOF MS calcd for 5 [M−H]⁺ calcd: 655.60, found: 656.00, [M+K]⁺ calcd: 693.60, found: 692.90. MALDI-TOF MS calcd for 6 [M+K]⁺ calcd: 819.50, found: 819.79.

Separation between 4 and 5 can be obtained by further flash column chromatography on the mixture of 2 and 3 followed by the same deprotection procedure mentioned above.

Scheme 3

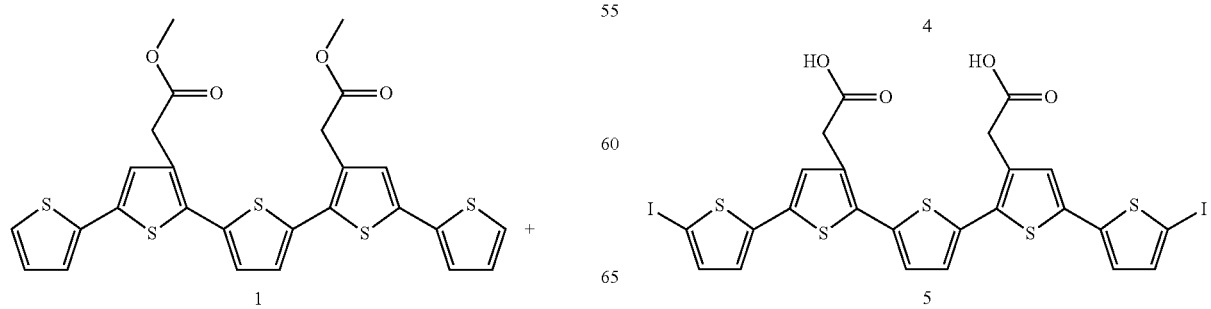

Example 6

Figure 7:
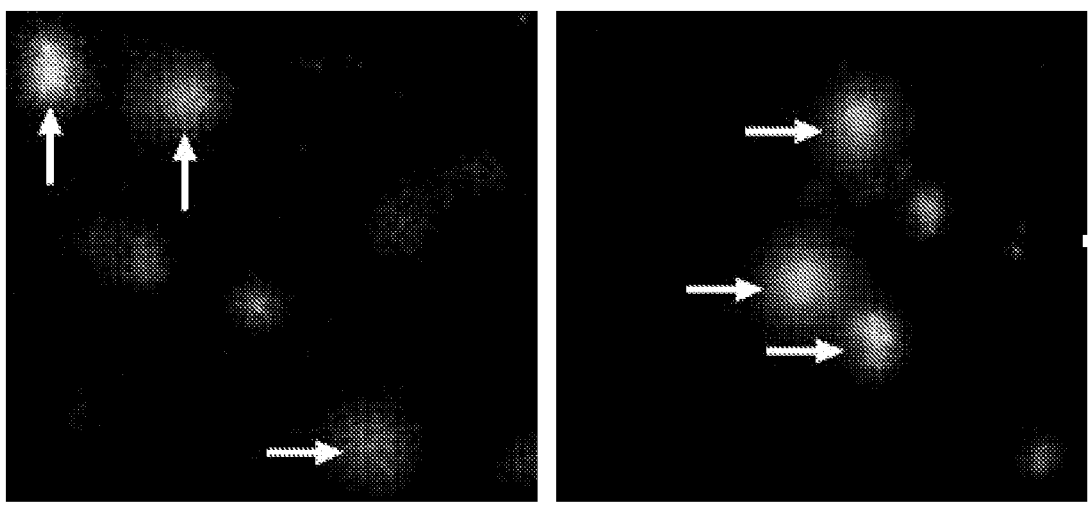
FIG. 7. Inventive compounds (left compound G and right compound F) bound to Aβ deposits in living mouse brain one week after injection.

Long Term In Vivo Effects Inventive Compound F and G in Transgenic Mice with Aβ Deposits Compounds G ((p-HTAA) and F (p-FTAA) were evaluated for long term in vivo effects on amyloid plaques using transgenic mice with AD-like pathology. The mice were prepared with cranial windows to allow direct monitoring of the brain surface with multiphoton spectroscopy. Compounds G and F were dissolved in aqueous PBS solution to 5 mg/ml. Both compounds were injected into the tail vein of the mice with the dose of 10 mg/kg. As mentioned above the compounds readily cross the blood brain barrier and bind to the AP deposits. One week after injection binding of the inventive compounds to AP deposits could still be observed (FIG. 7). This long lasting binding to the plaques is advantageous for a long term therapeutic effect of the inventive compounds.

Example 7

Example of Major Effects on β-amyloid Aggregation/Fibrillation by Inventive Compounds F and G This example describes the therapeutic effects of the inventive compounds F and G targeting diseases involving misfolding proteins.

Aβ peptide 1-42 was dissolved in hexafluoroisopropanol to a concentration of 1 mg/mL and further diluted to 20 μM in Tris-HCl 5 mM, 75 mM NaCl. The inventive compounds F and G were added in concentrations from 10 to 100 μM and the samples, including references without the inventive compounds, were incubated at 37° C. to initiate fibrillation. After 0h, 20 h and 66 h aliquots were withdrawn, deposited on formvar-carbon coated TEM grids and negatively stained using uranylacetate. A Phillips CM200 run at 200 kV was used to study the progress of fibrillation in the different samples.

Figure 1:
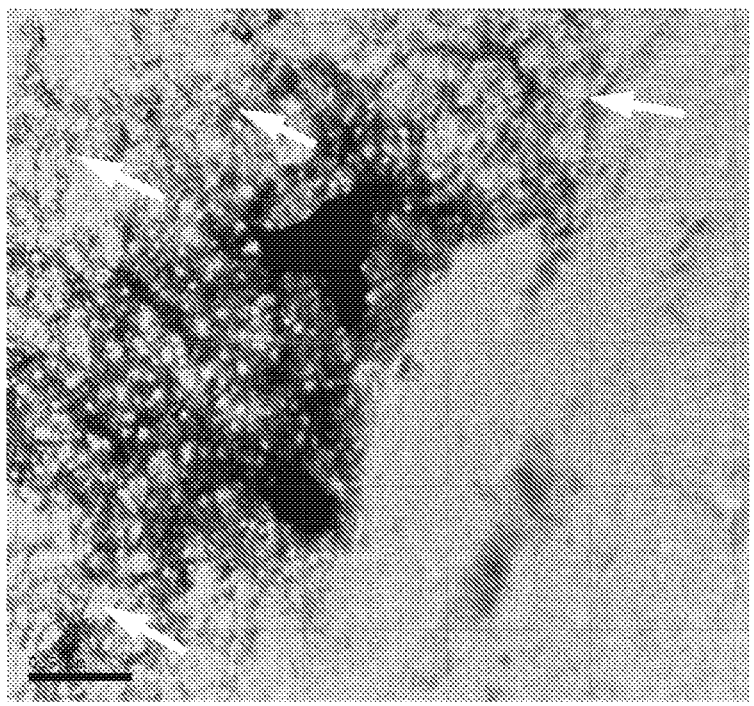
FIG. 1. Reference sample incubated 20 h, both scale bars represent 0.2 µm. Separated fibrils in sheet like aggregates marked by white arrows.
Figure 1:
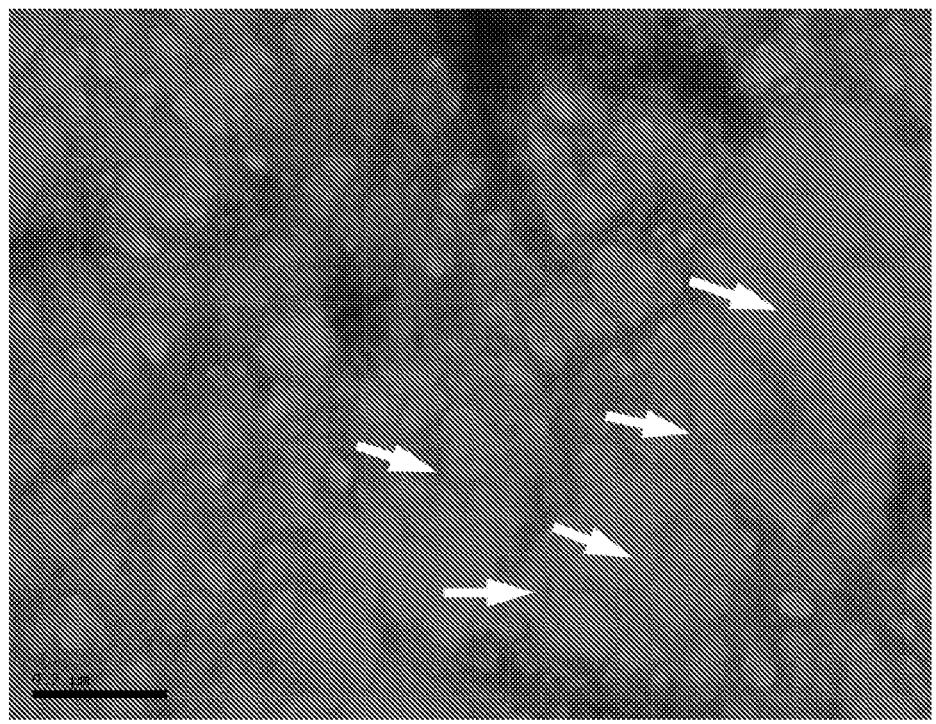
Figure 2:
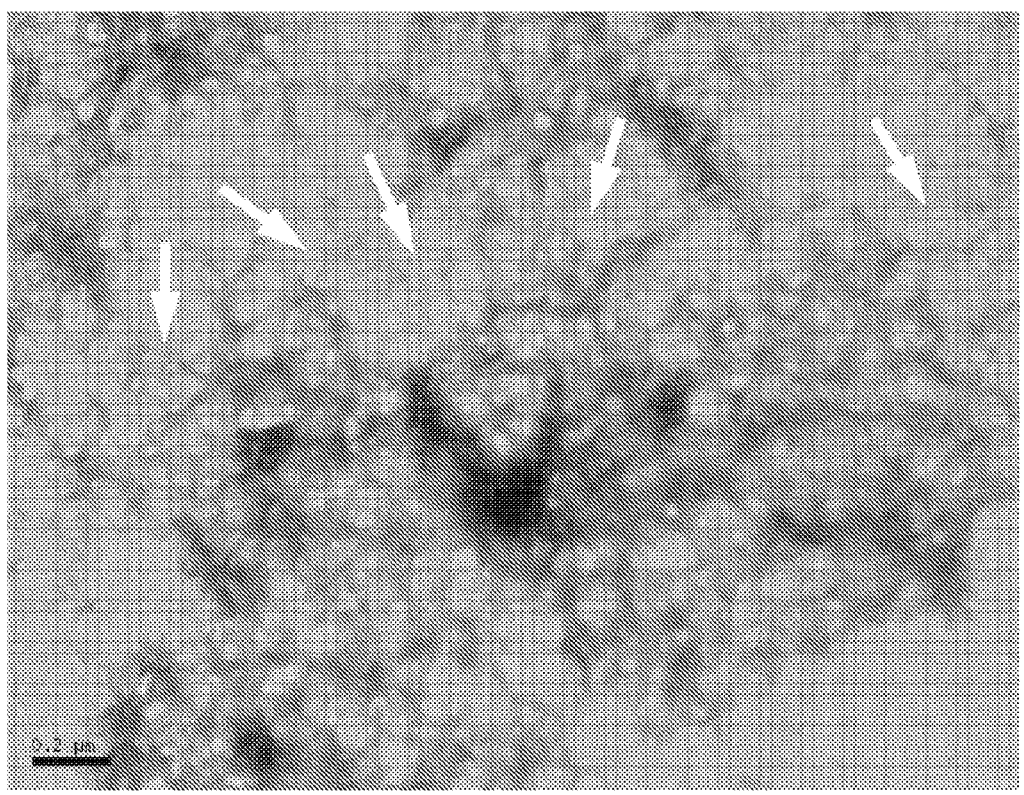
FIG. 2. Reference sample incubated 20 h, scale bar represent 0.2 µm. Separated fibrils in sheet like aggregates are seen in front of the white arrows.

The reference samples and samples with inventive compounds showed no fibrils or aggregated species prior to incubation at 37° C. (at 0h). After 20 h incubation the reference sample showed a high content of fibrils, assembled into sheets where separate fibrils could be visualized (see FIGS. 1 and 2). These aggregates were covering most of the TEM grid and no smaller fibril or oligomer like structures could be seen. After 66 h of incubation no major change in morphology compared to the 20 h samples could be seen, sheets with separate visible fibrils were found at high density on the grid, of a typical morphology illustrated in FIG. 3.

Figure 3:
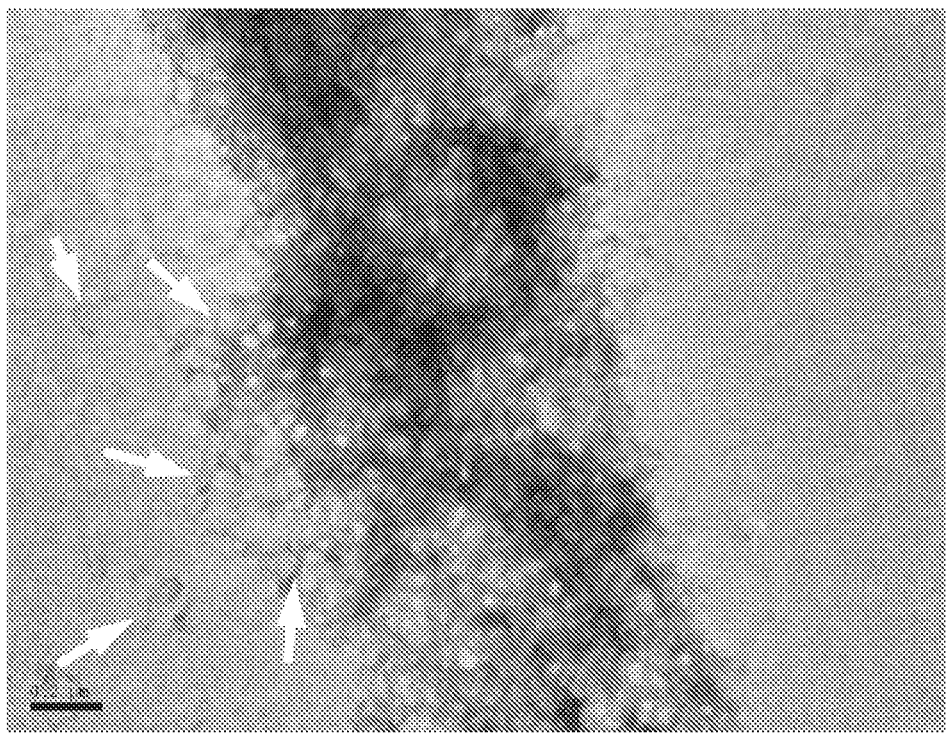
FIG. 3. Reference sample incubated 66 h, both scale bars represent 0.2 µm. White arrows are directed towards visible fibrils that are separated from the fibrillar sheets.
Figure 3:
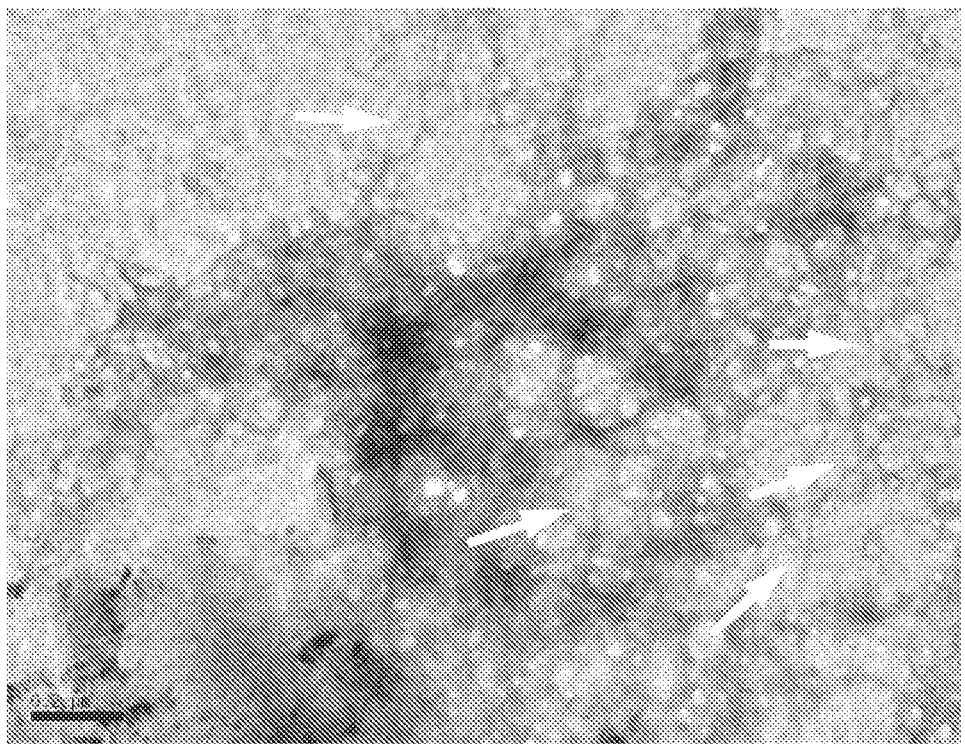
Figure 4:
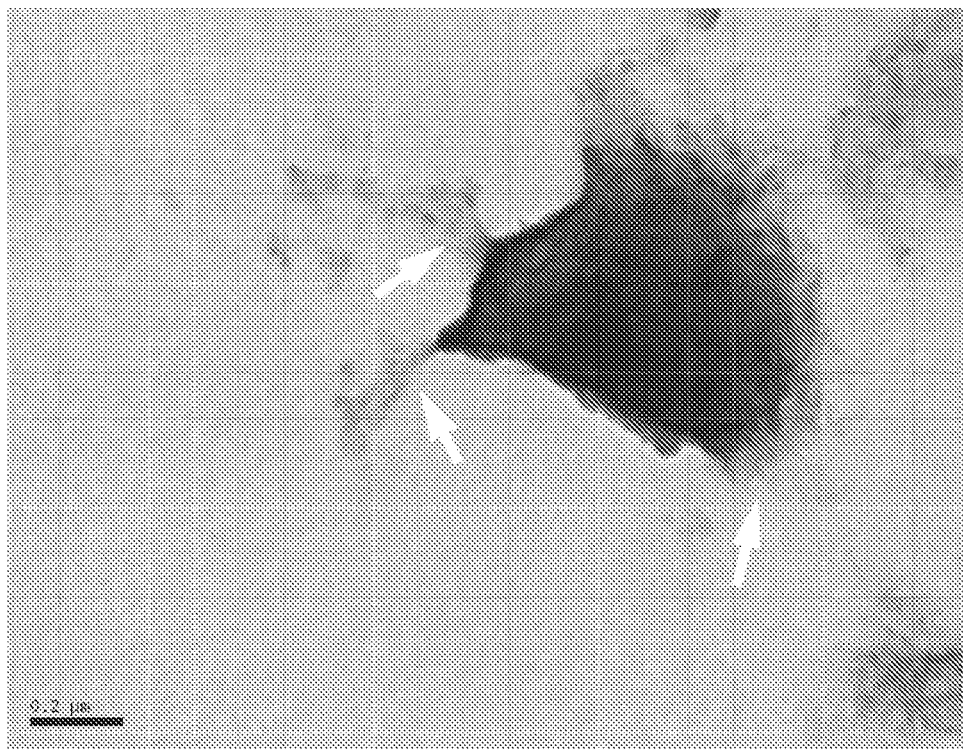
FIG. 4. Sample incubated with 100 uM of inventive compound F for 66 h. Scale bar represents 0.2 µm, both images have the same magnification. White arrows points towards dense aggregates where no fibrils can be seen.
Figure 4:
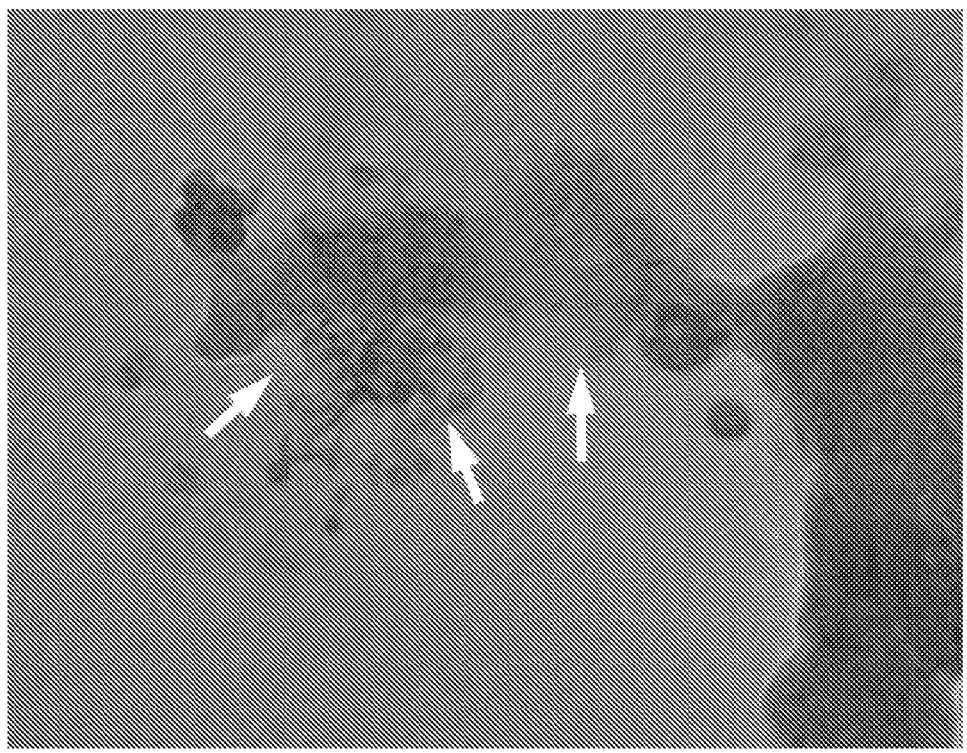

Samples incubated with 100 μM inventive compound F showed a distinctively different fibrillation process. After 20 h no dense aggregates resembling those in the reference sample (FIGS. 1 and 2) were found in the sample. After 66 h no separate fibrils could be found in the sample as could be found in the reference sample (FIG. 3). However very dense aggregates, with no distinguishable fibrils, were present, the typical morphology is illustrated in FIG. 4. This lack of fibrils in the sample after longer incubation times is significant of a major effect of compound F on the fibrillation of Aβ peptide 1-42.

Figure 5:
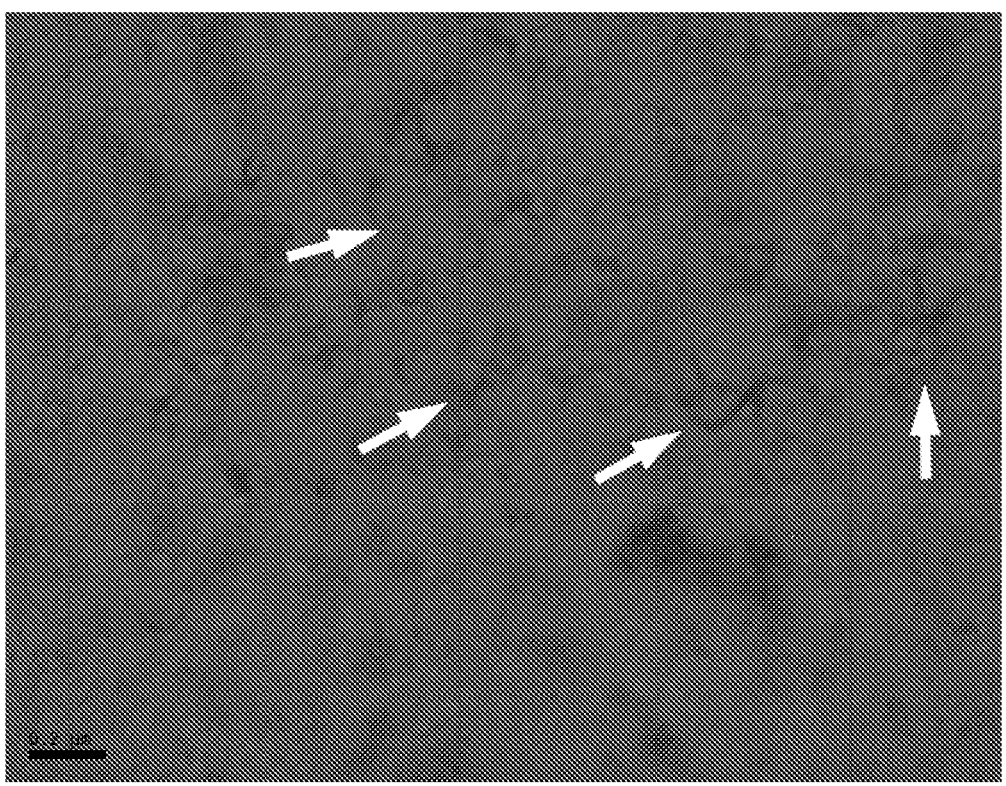
FIG. 5. Upper sample incubated with 100 uM of inventive compound G for 20 h. Scale bar represents 0.2 µm. Lower sample incubated with 10 uM of inventive compound G for 20 h. Scale bar represents 100 nm. Short branched fibrils is pointed out to the left while oligomer structures are pointed out to the right by white arrows.
Figure 5:
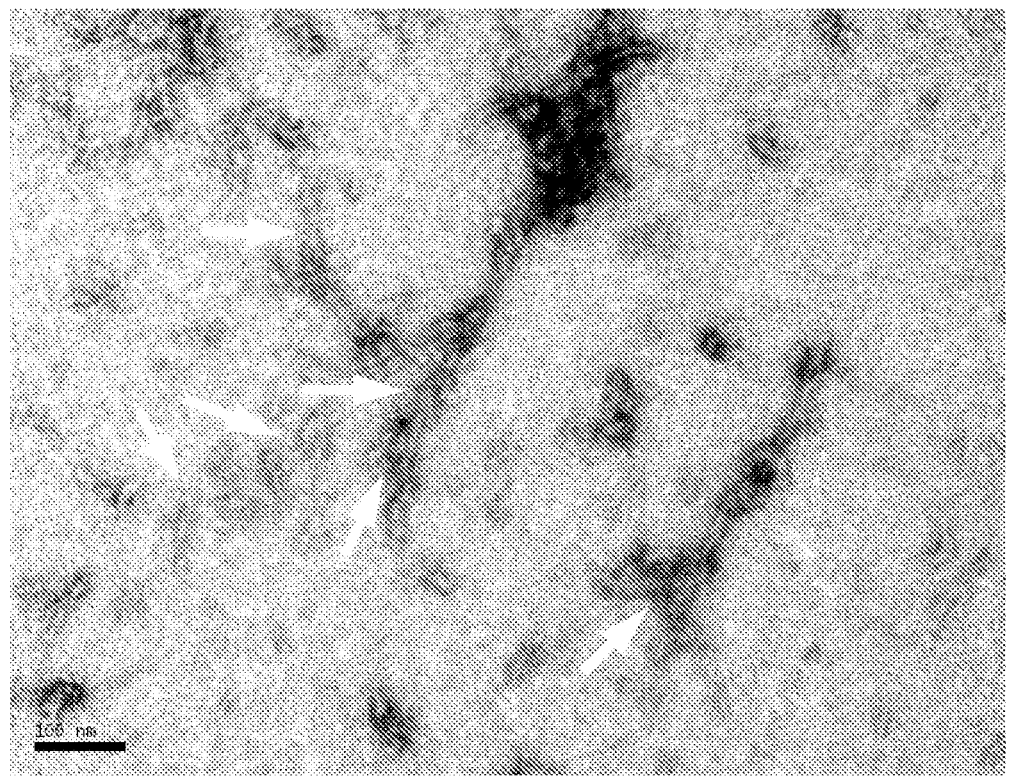
Figure 6:
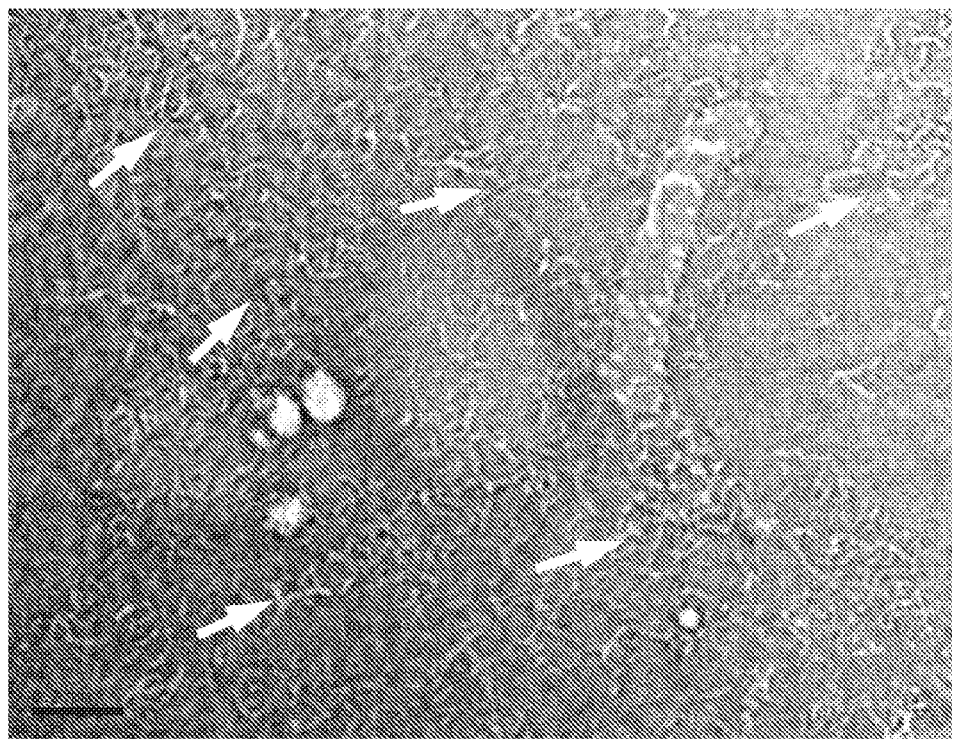
FIG. 6. Sample incubated with 100 uM of inventive compound G for 66 h. Scale bar represents 0.2 µm, both images have the same magnification. Short proto-fibrils are seen to the left while very dense aggregates with a typical morphology is seen to the right, indicated by white arrows.
Figure 6:
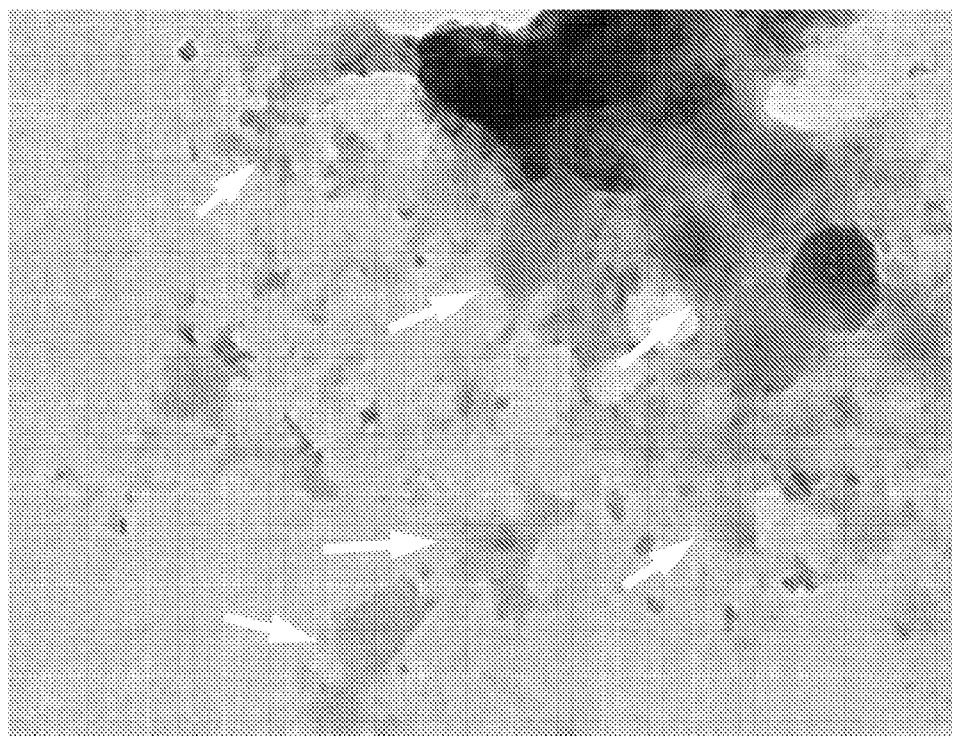

Samples incubated with 100 μM and 10 μM inventive compound G showed a distinctively different fibrillation process. After 20 h no dense aggregates resembling those in the reference sample (FIGS. 1 and 2) were found in the samples with 100 μM and 10 μM inventive compound G. A low density of short branched fibrils with a very low contrast was present in the sample with 100 μM G, illustrated in FIG. 5. In the sample with 10 μM inventive compound G a low density of oligomer like structures were found, illustrated in FIG. 5. After 66 h very few separate short proto-fibrils could be found in the sample with 100 μM G, illustrated in FIG. 6. More frequently very dense aggregates with a typical morphology illustrated in FIG. 6 were present. This lack of dense fibrils aggregates in the sample after both 20 and 66 h incubation time is significant of a major effect of compound G on the fibrillation of Aβ peptide 1-42.

Example 8

8.1 Effects of the p-FTAA Compound, 14 Days Treatment, in 4 Months Old Female hAPPSL Transgenic Mice: General Observations, Tolerance to Compound (Toxicity)

Vehicle: Phosphate Buffered Saline (PBS; 6.7 mM PO4, 155 mM NaCl, pH=7.3-7.5) (BioWhittaker PBS from Lonza).

T:I: p-FTAA, Mw=617 g/mol, diluted in vehicle from stock solution in deionized water (10 mg/ml).

Tg hAPPSL: Transgenic hAPPSL mice over-expressing hAPP(751) under the control of the murine Thy-1 promoter with a C57BL/6xDBA background.

Starting at 4 months of age, female hAPPSL mice were treated with vehicle only or p-FTAA in 3 dosages for 14 days. 40 hAPP Tg mice plus 4 reserves allocated to 4 different treatment groups were treated with either vehicle only (control) or with p-FTAA in dosages of 0.1 mg/kg/day, 1 mg/kg/day, or 10 mg/kg/day. Vehicle and T.I.s were administered twice daily intra peritoneal (ip) for 14 days.

In total 44 animals allocated to 4 treatment groups were included in the study. 4 animals died premature due to unknown reason: 1 animal each of the 1 mg/kg and 10 mg/kg T.I. groups and 2 animals from the control group. Dead animals cannot be attributed to p-FTAA, as most of the deaths were found in the vehicle group.

8.2 Effects of the p-FTAA Compound, 14 Days Treatment, in 4 Months Old Female hAPPSL Transgenic Mice: Biodistriubtion Vehicle: Phosphate Buffered Saline (PBS; 6.7 mM PO4, 155 mM NaCl, pH=7.3-7.5) (BioWhittaker PBS from Lonza).

T:I: p-FTAA, Mw=617 g/mol, diluted in vehicle from stock solution in deionized water (10 mg/ml).

Tg hAPPSL: Transgenic hAPPSL mice over-expressing hAPP(751) under the control of the murine Thy-1 promoter with a C57BL/6xDBA background.

Starting at 4 months of age, female hAPPSL mice were treated with vehicle only or p-FTAA in 3 dosages for 14 days. 40 hAPP Tg mice plus 4 reserves allocated to 4 different treatment groups were treated with either vehicle only (control) or with p-FTAA in dosages of 0.1 mg/kg/day, 1 mg/kg/day, or 10 mg/kg/day. Vehicle and T.I.s were administered twice daily intra peritoneal (ip) for 14 days.

The biodistribution of p-FTAA in the mice was assessed by determining the parent compound in the right brain hemisphere (without cerebellum), liver, kidney, and plasma of the treated animals. p-FTAA was determined in all the matrices by different bioanalytical methods involving HPLC-MS/MS. Each method was characterized in terms of specificity, linearity, accuracy and precision in order to give reliable results.

Tissue Sampling: After the last treatment, animals were sacrificed. Each treatment group was divided in 3 sampling points resulting in 3-4 animals per sampling point per group (time points below refer to the time point of CSF sampling):

1) Immediately before last dosing on day 14 (predose)
2) 0.5 hours after last dosing on day 14
3) 3 hours after last dosing on day 14

From each animal, CSF, blood, brains, liver, and kidney were collected. Therefore, mice were sedated by standard inhalation anesthesia (Isofluran, Baxter)

The results showed that the animals were exposed systemically to p-FTAA at all dose levels. The brain p-FTAA levels demonstrated that p-FTAA crossed the blood-brain barrier after ip administration. Significant exposure to p-FTAA was also observed in the liver and in the kidney with the highest levels being quantified in the latter organ. The presence of the drug in the kidney and in the liver suggested that both hepatic oxidative processes and renal clearance are involved in the systemic clearance of the drug. The high concentration of the drug in the kidney also suggested that urinary excretion is the main elimination route of systemic p-FTAA. The levels of p-FTAA were higher in the kidney compared to the liver suggesting that renal clearance is a major elimination route for the drug. The presence of the drug in the liver suggests that also liver metabolic processes (Phase I and II) significantly contributed to the total systemic clearance of the compound.

8.3 Effects of the p-FTAA Compound, 30 Days Treatment, in 8 Months Old Female hAPPSL Transgenic Mice: Results of Human Aβ Determinations in Brain Samples Vehicle: Phosphate Buffered Saline (PBS; 6.7 mM PO4, 155 mM NaCl, pH=7.3-7.5) (BioWhittaker PBS from Lonza).

T:I: p-FTAA, Mw=617 g/mol, diluted in vehicle from stock solution in deionized water (10 mg/ml).

Tg hAPPSL: Transgenic hAPPSL mice over-expressing hAPP(751) under the control of the murine Thy-1 promoter with a C57BL/6xDBA background.

Starting at 8 months of age, female hAPPSL mice were treated with vehicle only or p-FTAA in 3 dosages for 30 days. The Test Item (T.I.) p-FTAA was administered in 3 dosages in Vehicle. 48 hAPP Tg mice plus 4 reserves allocated to 4 different treatment groups were treated with either vehicle only (control) or with p-FTAA in dosages of 0.1 mg/kg/day, 1 mg/kg/day, or 10 mg/kg/day. As an additional control, 12 nTg littermates of the hAPPSL mice (plus 1 reserve) were treated with vehicle only. Vehicle and T.I.s were administered twice daily intra peritoneal (i.p.) for 30 days.

Human Aβ38, Aβ40 and Aβ42 were determined in homogenates of the left brain hemispheres and in CSF samples of all Tg animals by an immunosorbent assay from Mesoscale Discovery p-FTAA treatment in the highest dose (10 mg/kg/day) led to significantly decreased Aβ38, Aβ40 and Aβ42 levels in the CSF as well as in the SDS brain homogenate fraction.

Treatment 48 hAPP Tg mice plus 4 reserves allocated to 4 different treatment groups were treated with either vehicle only (control) or p-FTAA. As an additional control, 12 nTg littermates of the hAPPSL mice (plus 1 reserve) were treated with vehicle only. Compound and vehicle were administered twice daily i.p. for 30 days as shown in the table below. Tg hAPPSL mice with a C57BL/6xDBA background and corresponding nTg littermates at an age of 8 months (±2 weeks) were randomly assigned to the treatment groups.

| Group | Number of animals | Type of animals | Sex | Age at start | Treatment Substance | Dose | Administration | Tissues sampled |
|---|---|---|---|---|---|---|---|---|
| A | 12 | Tg hAPPSL mice | f | 8 months ± 2 weeks | Vehicle | — | i.p. twice daily for 30 days | plasma, CSF, brain |
| B | 12 | Tg hAPPSL mice | f | 8 months ± 2 weeks | p-FTAA | 0.1 mg/kg/day | i.p. twice daily for 30 days | plasma, CSF, brain |
| C | 12 | Tg hAPPSL mice | f | 8 months ± 2 weeks | p-FTAA | 1 mg/kg/day | i.p. twice daily for 30 days | plasma, CSF, brain |
| D | 12 | Tg hAPPSL mice | f | 8 months ± 2 weeks | p-FTAA | 10 mg/kg/day | i.p. twice daily for 30 days | plasma, CSF, brain |
| E | 12 | nTg hAPPSL mice | f | 8 months ± 2 weeks | Vehicle | — | i.p. twice daily for 30 days | plasma, CSF, brain |

Brain Protein Extraction

Left hemi-brain samples (without cerebellum) of Tg animals were homogenized and separated. SDS fraction was prepared, after thawing, hemispheres were homogenized with the Homogenizer "Ultra Turrax T8" at highest speed in TBS (20 mM Tris, 137 mM NaCl, pH=7.6; containing protease inhibitor cocktail; 100 mg brain wet weight per ml TBS). One aliquot (1 ml) was centrifuged (74,200×g for 1 h at 4° C.). The pellets were suspended in 1 ml SDS (2% SDS in Aqua bidest), centrifuged as above and the supernatants were kept at −20° C. (SDS fraction).

Determination of Aβ Species

In the brain homogenate SDS fraction and in CSF of each Tg mouse, human Aβ38, Aβ40 and Aβ42 levels were measured with a Aβ-kit from Mesoscale Discovery. Aβ levels were evaluated in comparison to a peptide standard as pg/mg brain (wet weight) or pg/ml CSF.

Statistics for Biochemical Parameters

Descriptive statistical analysis was performed on all evaluated parameters. Data were represented as mean±standard deviation (SD). Grubb's test was used to detect outliers. Normality distribution of the values was tested with Kolmogorov Smirnov normality distribution test. Group differences between all Tg groups were calculated by a parametric ANOVA followed by a Bonferroni post test.

Aβ Levels in CSF Samples

Figure 8A:
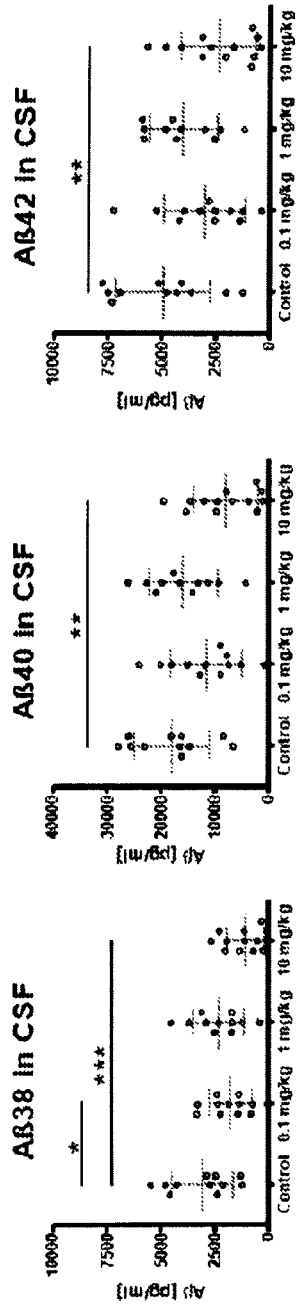
FIG. 8

Human Aβ38, Aβ40 and Aβ42 levels were measured in CSF samples of each Tg mouse with an immunosorbent assay. In the hAPPSL mice, CSF levels of Aβ40 typically exceed those of Aβ42 and Aβ38. All 3 analytes were affected by a treatment with p-FTAA. Mean Aβ38, Aβ40 and Aβ42 levels were highest in the vehicle treated group and lowest in the animals treated with 10 mg/kg/day. Compared to the vehicle group, the CSF Aβ lowering effect of a 10 mg/kg/day p-FTAA treatment was highly significant in an One-Way ANOVA (p<0.001 for Aβ38 and p<0.01 for Aβ40 and Aβ42). Animals treated with 0.1 mg/kg/day showed also lower mean Aβ levels but statistical significance was observed for Aβ38 only. The group receiving 1 mg/kg/day p-FTAA did not differ significantly from the vehicle control. (FIG. 8(A))

Aβ Levels in Brain Samples

Figure 8B:
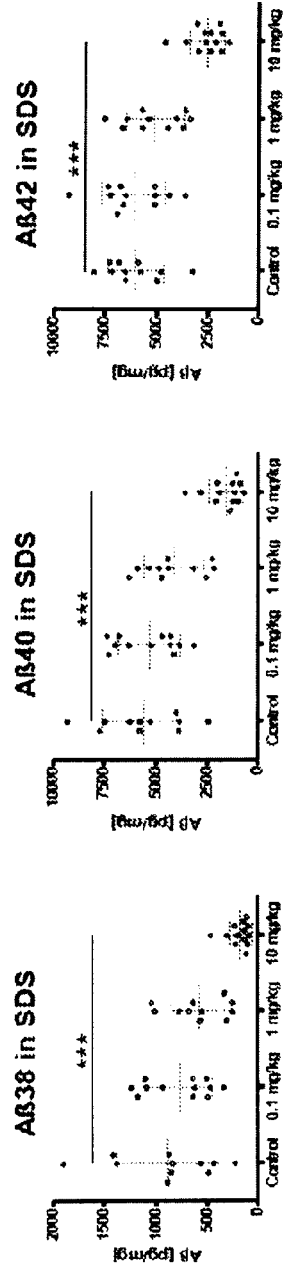

Aβ was extracted sequentially from the brain with solvents of increasing power: SDS. Human Aβ38, Aβ40, and Aβ42 levels were measured in the SDS fraction of each Tg mouse with an immunosorbent assay. (FIG. 8(B))

For the Aβ levels in the SDS fractions significant group differences were observed: Mean Aβ levels were highest in the vehicle treated group and lowest in for the animals treated with 10 mg/kg/day. The difference of the mean Aβ38, Aβ40 and Aβ42 levels between the vehicle control group and the 10 mg/kg/day group were highly significant (p<0.001). Beside the lower means, the intra group variability for the 10 mg/kg/day group was very low, which can be interpreted as another sign of T.I. affectivity.

Treatment with the highest dosages (10 mg/kg/day) of p-FTAA significantly decreased Aβ38, Aβ40 and Aβ42 levels in the CSF and in the SDS brain homogenate fraction.

We also noted, data not shown, that p-FTAA treatment for 14 days, in 4 months old female hAPPSL transgenic mice, led to decreased Aβ38, Aβ40 or Aβ42 levels in the DEA Extraction of [soluble] Amyloid beta from brain homogenates. The effect was strongest for 10 mg/kg/day group.

8.4 Effects of the p-FTAA Compound, 30 Days Treatment, in 8 Months Old Female hAPPSL Transgenic Mice: Morris Water Maze (MWM) Test Vehicle: Phosphate Buffered Saline (PBS; 6.7 mM PO4, 155 mM NaCl, pH=7.3-7.5) (BioWhittaker PBS from Lonza).

T:I: p-FTAA, Mw=617 g/mol, diluted in vehicle from stock solution in deionized water (10 mg/ml).

Tg hAPPSL: Transgenic hAPPSL mice over-expressing hAPP(751) under the control of the murine Thy-1 promoter with a C57BL/6xDBA background.

Starting at 8 months of age, female hAPPSL mice were treated with vehicle only or p-FTAA in 3 dosages for 30 days. The Test Item (T.I.) p-FTAA was administered in 3 dosages in Vehicle. 48 hAPP Tg mice plus 4 reserves allocated to 4 different treatment groups were treated with either vehicle only (control) or with p-FTAA in dosages of 0.1 mg/kg/day, 1 mg/kg/day, or 10 mg/kg/day. As an additional control, 12 nTg littermates of the hAPPSL mice (plus 1 reserve) were treated with vehicle only. Vehicle and T.I.s were administered twice daily intra peritoneal (i.p.) for 30 days.

The MWM was performed during 4 days at the end of treatment period (treatment days 24 to 27). A circular pool (100 cm diameter) filled with tap water with a temperature of 21±2° C. was virtually divided into four quadrants. A transparent platform (8 cm diameter) was placed about 0.5 cm beneath the water surface. During the whole test session, except the probe trial, the platform was located in the southwest quadrant of the pool.

Each mouse had to perform three swimming trials on each of four consecutive days. A single trial lasted for a maximum of one minute. During this time, the mouse had the chance to find the hidden, diaphanous target. If the animal did not find the "way" out of the water, the investigator guided to or placed the mouse on the platform. After each trial, the mouse was allowed to rest on the platform for 10-15 seconds to orientate in the surrounding. On the walls surrounding the pool, posters with black, bold geometric symbols (e.g. a circle and a square) were fixed which the mice could use as landmarks for spatial orientation.

The escape latency (the time needed to find the hidden platform and therefore to escape from the water), the swimming path (the length to reach the target), the swimming speed and in the probe trial crossings over the former platform position and the abidance in the target quadrant were evaluated. A computerized tracking system with a camera above the center of the pool was used for the measurements.

Animals with a swimming speed below 0.08 m/s in one of the trials were identified as floater, excluded from statistical analysis of all trials, and were not displayed in the graphs.

Statistics for MWM Parameters

Descriptive statistical analysis was performed on all evaluated parameters. Data were represented as mean±standard error of mean (SEM). Grubb's test was used to detect outliers. Normality distribution of the values was tested with Kolmogorov Smirnov normality distribution test. Group differences were calculated by a parametric ANOVA followed by a Bonferroni post test or by a non-parametric Kruskal Wallis ANOVA followed by a Dunn's post test if Gaussian distribution was missing. Learning curves were evaluated by a Two-way ANOVA followed by a Bonferroni post test. Vehicle treated Tg animals (Group A) were used as the control group.

Mice treated with 10 mg/kg p-FTAA showed a better performance than any other Tg group in terms of the swimming path (FIG. 9).

8.5 Effects of the p-FTAA Compound, 30 Days Treatment, in 8 Months Old Female hAPPSL Transgenic Mice: Plaque Load Vehicle: Phosphate Buffered Saline (PBS; 6.7 mM PO4, 155 mM NaCl, pH=7.3-7.5) (BioWhittaker PBS from Lonza).

T:I: p-FTAA, Mw=617 g/mol, diluted in vehicle from stock solution in deionized water (10 mg/ml).

Tg hAPPSL: Transgenic hAPPSL mice over-expressing hAPP(751) under the control of the murine Thy-1 promoter with a C57BL/6xDBA background.

Starting at 8 months of age, female hAPPSL mice were treated with vehicle only or p-FTAA in 3 dosages for 30 days. The Test Item (T.I.) p-FTAA was administered in 3 dosages in Vehicle. 48 hAPP Tg mice plus 4 reserves allocated to 4 different treatment groups were treated with either vehicle only (control) or with p-FTAA in dosages of 0.1 mg/kg/day, 1 mg/kg/day, or 10 mg/kg/day. As an additional control, 12 nTg littermates of the hAPPSL mice (plus 1 reserve) were treated with vehicle only. Vehicle and T.I.s were administered twice daily intra peritoneal (i.p.) for 30 days.

Following blood sampling, mice were transcardially perfused with physiological (0.9%) saline. The brains were removed from the skull and the cerebellum was cut off, immediately frozen on dry ice and stored at −80° C. The remaining brain was hemisected and the left hemisphere was weighed, immediately frozen on dry ice and stored at −80° C. until A13 analysis. The right hemisphere was fixed with paraformaldehyde as described in section 4.3.1.

The right hemispheres of all Tg mice were fixed by immersion in freshly prepared 4% paraformaldehyde/PBS (pH 7.4) for one hour at room temperature. Thereafter brains were transferred to a 15% sucrose PBS solution for 24 hours to ensure cryoprotection. On the next day, brains were frozen in isopentane and stored at −80° C. until used for histological analysis.

From 6 animals per Tg group, 15 cryo-sections per layer (altogether 5 layers), each 10 µm thick (Leica CM 3050S) were sagittally cut. Brain levels were chosen according to the morphology atlas "The Mouse Brain" from Paxinos and Franklin (2nd edition). The cutting of the five levels started with a random slice corresponding to FIG. 105 (total appearance of the dentate gyrus), then sampling was continued uniformly and systematically, always retaining 15 slices per level in series and discarding 100 µm in between the levels.

Plaque load was quantified by staining with 6E10 IHC directed against AA1-17 of the human amyloid peptide and ThioflavinS staining against beta-sheet structures in a double incubation. Tissues of all investigated animals were handled uniformly.

Statistics for Histological Parameters

Descriptive statistical analysis was performed on all evaluated parameters. Data were represented as mean±standard error of mean (SEM). Outliers were detected by Grubbs' test and were excluded from statistical analyses.

Values of the five single measurements (one from each cut level) per animal were integrated to one value per animal (individual mean). Group means were calculated with these integrated values. After Kolmogorov Smirnov normality distribution tests differences were calculated by a parametric ANOVA followed by a Newman Keuls multiple comparison post-hoc test or by a non-parametric Kruskal Wallis ANOVA followed by a Dunn's Multiple comparison test, if Gaussian distribution was missing.

FIG. 10 indicate the major effect of p-FTAA treatment in the hippocampus without significant changes in the cortex. With regards to the different plaque load development in cortex and hippocampus of this mouse model, this perfectly fits to the concept of an aggregation inhibiting compound the hippocampal plaque area percentage in the p-FTAA treated mice is reduced compared to the vehicle control (FIG. 10). Statistical significance for this effect due to a decrease of mean plaque size was demonstrated for the 1 mg/kg and 10 mg/kg p-FTAA treated mice by a t-test. Although the treatment period was only 30 days, a 40% decrease in plaque area was achieved for the 1 mg/kg treated animals.

In accordance with the reduced AP levels in the SDS brain homogenate fraction, treatment with p-FTAA led to a reduction of plaque load. This was mainly visible in the hippocampus, where plaques are less mature than in the cortex. The effect was observed with 6E10 IHC against human amyloid as well as with ThioflavinS stainings of beta-sheet cores located in the centre of plaques. The reduction of more diffuse 6E10 IR surrounding the plaque-cores was strongest for the 10 mg/kg p-FTAA treatment whereas the strongest effect on beta-sheet cores was observed for the 1 mg/kg p-FTAA treatment.

8.6 Effect of Two Substances on Aβ1-42 Induced Lesions in Primary Chicken Neurons: Neuroprotectivity T:I 1: p-HTAA, Mw=529 g/mol, diluted in vehicle from stock solution in PBS+1.33% DMSO (10 mg/ml).

T:I 2: POWT-13, Mw=2782 g/mol, diluted in vehicle from stock solution in deionized water (40 mg/ml).

Cell source: Telencephalon neurons from 8-day-old chicken embryos (Lohman Brown hybrid)

Nutrition medium: DMEM with 4.5 g glucose/l, 5% Nu Serum, 0.01% gentamycin, 2 mM L-glutamine Group size: n=6 for each T.I. and R.I. concentration per experiment Lesion: 10 µM Aβ1-42 (pre-aggregated for 48 h) at DIV8 for 48 h Evaluation of the effects: MTT on DIV 10

Duration of one single experiment: 9 days

Number of independent experiments per assay: n=2

Preparation of Chicken Telencephalon Neurons

One-day-old fertilized eggs will be stored under appropriate conditions until start of breeding. On embryonic day 0 eggs will be transferred to the breeding incubator and under turning kept at 37.8° C. and 55% humidity until embryonic day eight. All cell culture experiments will be carried out under sterile conditions meaning all procedures will be performed in a cell culture unit with special cell culture equipment. Items necessary like glassware, forceps or scissors will be sterilised prior to the experiment. Stock solutions will be purchased already sterile and final suspensions like the culture medium will be freshly prepared in the laminar airflow cabinet. Neurons preparation in short, embryos will be transferred to a plastic dish, and decapitated. Both hemispheres will be removed, collected and cleaned from any loose tissue. Hemispheres will be mechanically dissociated and $4.8 \times 10^4$ cells will be plated out in each well in a volume of 160 µl. The cell culture medium for chicken telencephalon neurons consists of DMEM with 4.5 g glucose/l, 5% Nu Serum, 0.01% gentamycin and 2 mM L-glutamine. Cultures will be maintained at 37° C., 95% humidity and 5% $CO_2$.

Aggregation of Aβ1-42

Aβ1-42 peptides will be dissolved in 0.25% $NH_3$ to a final concentration of 1 mM. The dissolved Aβ1-42 peptides will then be diluted with PBS to a final concentration of 255 µM and incubated for 48 h at 37° C. After 48 h of aggregation, Aβ1-42 peptides will be sonicated for 1 minute in an ultrasonic water bath (in both cases, when Aβ1-42 peptides are aggregated together or separately from test items).

MTT-Viability Assay

Viability of cultures will be determined with the MTT assay using a plate-reader (570 nm) as described e.g. in SOP MET004. The MTT-assay is based on the reduction of yellow MTT (3-(4,5-dimethylthiazol-2-yl)-2,5,diphenyl tetrazolium bromide), to dark blue formazan crystals by mitochondrial dehydrogenases (succinate dehydrogenase). Since this reaction is catalysed in living cells only this assay can be used for the quantification of cell viability. For determination of cell viability, MTT solution is added to each well in a final concentration of 0.5 mg/ml. After 2 hours the MTT containing medium is aspired. Cells are lysed with 3% SDS and formazan crystals are dissolved in isopropanol/HCl. To estimate optical density, a plate-reader (Anthos HT II or pquant) is used at wavelength 570 nm. Cell viability is expressed in optical density (OD).

Application of Test and Reference Items in Aβ1-42 Lesions

At DIV8, pre-aggregated Aβ1-42 will be applied at a final concentration of 10 µM for 48 h. T.I. will be applied:

1) directly to Aβ1-42 at the start of aggregation in PBS (DIVE); after 48 h of aggregation on DIV8, pre-aggregated Aβ1-42 in the presence of test item will be applied on cells for 48 hours or 2) with pre-aggregated Aβ1-42 on chicken neurons (DIV8) for 48 hours The reference item will only be applied to cultures together with pre-aggregated Aβ1-42 (point 2) but will not be added directly to Aβ1-42 at the start of aggregation (point 1).

After 48 hours of incubation of T.I. and Aβ1-42 on cells (DIV10), viability of neurons will be analysed by the MTT assay.

Controls

The following controls were used:
1) Vehicle control (for each test item and reference item)
2) Aβ1-42 without test item and reference item
3) 10 μM T.I. only (not shown)

Results

Test items (T.I.s) and already pre-aggregated Aβ1-42 applied on neurons simultaneously gives the results as shown in FIG. 11. Both compounds results in better viability compared to 10 μM Aβ1-42 alone. Stoichiometric ratios of T.I. to 10 M Aβ1-42 is shown beneath the graph.

Test items (T.I.s) added to Aβ1-42 during aggregation gives the results shownb in FIG. 12. Both compounds results in better viability compared to 10 μM Aβ1-42 alone. Stoichiometric ratios of T.I. to 10 μM Aβ1-42 is shown beneath the graph.

The invention claimed is:

1. A compound of the formula

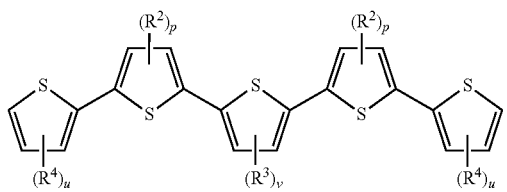

wherein each u is independently selected from 0 and 1;

each $R^2$ and $R^4$ is independently selected from carboxy, carboxyalkyl, alkoxycarbonylalkyl, aminoalkyl, (amino)(carboxy)alkyl and (amino)(carboxy)alkoxy;

or a pharmaceutically acceptable salt thereof.

2. The compound according to claim 1, wherein each $R^2$ is independently selected from carboxyalkyl, alkoxycarbonylalkyl, aminoalkyl, (amino)(carboxy)alkyl and (amino)(carboxy)alkoxy.

3. The compound according to claim 1, wherein each $R^4$ is carboxy.

4. The compound according to claim 1, wherein each u=1.

5. The compound according to claim 1, wherein the compound is

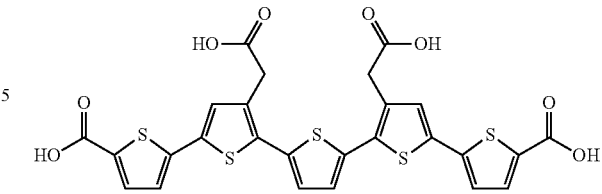

or a pharmaceutically acceptable salt thereof.

6. The compound according to claim 1, wherein the compound is

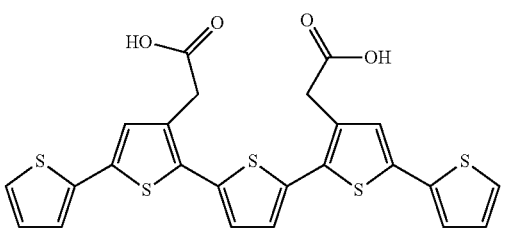 [SMILES: O=C(O)Cc1cc(-c2cccs2)sc1-c1ccc(-c2sc(-c3cccs3)cc2CC(=O)O)s1]

or a pharmaceutically acceptable salt thereof.

7. The compound according to claim 1, wherein the compound is

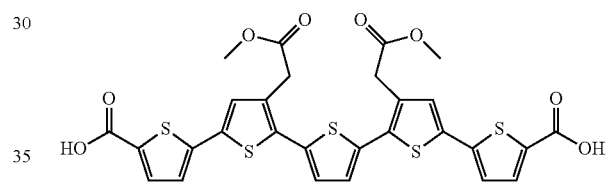

or a pharmaceutically acceptable salt thereof.

8. The compound according to claim 1, wherein the compound is

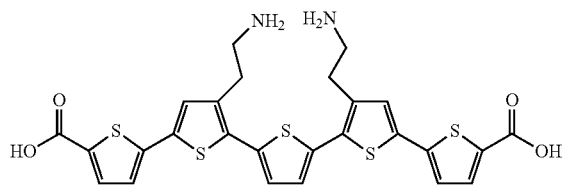 [SMILES: NCCc1cc(-c2ccc(C(=O)O)s2)sc1-c1ccc(-c2sc(-c3ccc(C(=O)O)s3)cc2CCN)s1]

or a pharmaceutically acceptable salt thereof.

* * * * *

UNITED STATES PATENT AND TRADEMARK OFFICE
CERTIFICATE OF CORRECTION

PATENT NO. : 8,710,246 B2
APPLICATION NO. : 13/124621
DATED : April 29, 2014
INVENTOR(S) : Peter Asberg, Leif Johansson and Anna Herland It is certified that error appears in the above-identified patent and that said Letters Patent is hereby corrected as shown below:

Title page, Item 57 (Abstract), delete the structure and replace with:

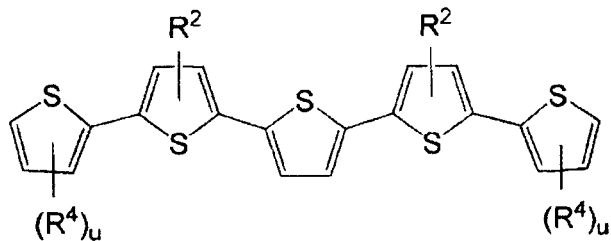

In the Claims

In Claim 1, Column 43, Lines 25 to 33, delete the structure and replace with:

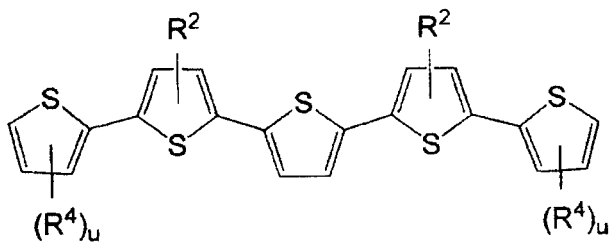

Signed and Sealed this
Eighteenth Day of August, 2015

Michelle K. Lee
*Director of the United States Patent and Trademark Office*

UNITED STATES PATENT AND TRADEMARK OFFICE
CERTIFICATE OF CORRECTION

PATENT NO. : 8,710,246 B2  
APPLICATION NO. : 13/124621  
DATED : April 29, 2014  
INVENTOR(S) : \Asberg et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 160 days.

Signed and Sealed this

Twenty-ninth Day of September, 2015

Michelle K. Lee

*Director of the United States Patent and Trademark Office*